United States Patent
Augarten et al.

(10) Patent No.: US 8,939,888 B2
(45) Date of Patent: Jan. 27, 2015

(54) METHOD AND SYSTEM FOR DETERMINING THE PRESSURE OF A FLUID IN A SYRINGE, AN ACCESS PORT, A CATHETER, AND A GASTRIC BAND

(75) Inventors: Mike Augarten, Goleta, CA (US); Sean Snow, Carpinteria, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 503 days.

(21) Appl. No.: 13/101,952

(22) Filed: May 5, 2011

(65) Prior Publication Data

US 2011/0270027 A1    Nov. 3, 2011

Related U.S. Application Data

(63) Continuation-in-part of application No. 12/769,516, filed on Apr. 28, 2010, now abandoned.

(51) Int. Cl.
*A61M 5/48* (2006.01)
*A61F 5/00* (2006.01)
*A61M 5/31* (2006.01)

(52) U.S. Cl.
CPC .............. *A61M 5/486* (2013.01); *A61F 5/0043* (2013.01); *A61F 5/0056* (2013.01); *A61M 2005/3125* (2013.01); *A61M 2205/3569* (2013.01); *A61M 2205/3592* (2013.01); *A61M 2205/505* (2013.01); *A61M 2205/52* (2013.01)
USPC .......................................................... 600/37

(58) Field of Classification Search
USPC ..................... 600/37, 561; 606/157; 604/909
See application file for complete search history.

(56) References Cited

U.S. PATENT DOCUMENTS

| | | | |
|---|---|---|---|
| 2,163,048 | A | 6/1939 | McKee |
| 3,667,081 | A | 6/1972 | Burger |
| 3,840,018 | A | 10/1974 | Heifetz |
| 4,117,727 | A | 10/1978 | Friswell et al. |
| 4,118,805 | A | 10/1978 | Reimels |
| 4,157,713 | A | 6/1979 | Clarey |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Bio Enterics Lap-Band Adjustable Gastric Banding System, Inamed Health, pub. 18007 Aug. 28, 2003, pp. 1-115.

*Primary Examiner* — Christine Matthews
(74) *Attorney, Agent, or Firm* — Gordon & Jacobson, PC

(57) ABSTRACT

A method and system for determining pressure in a syringe, and more specifically to a syringe pressure accessory which can be connected to a syringe to determine pressure in a syringe and a gastric band. The syringe pressure accessory can detect a pressure of a syringe and/or a gastric band and digitally display the pressure. The syringe pressure accessory can include a durable unit and a disposable unit. The disposable unit can be disposed of after a single use, while the durable unit can be reused with multiple disposable units. The syringe pressure accessory can also include a syringe attachment unit and one or more display units for a caretaker or a patient. The display unit can be wirelessly connected to the syringe attachment unit to display a pressure chart or the results of various analysis of the pressure data. Markers can be added to the pressure chart.

8 Claims, 15 Drawing Sheets

(56) References Cited

U.S. PATENT DOCUMENTS

| | | |
|---|---|---|
| 4,286,584 A | 9/1981 | Sampson et al. |
| 4,370,982 A | 2/1983 | Reilly |
| 4,592,339 A | 6/1986 | Kuzmak et al. |
| 4,592,355 A | 6/1986 | Antebi |
| 4,601,713 A | 7/1986 | Fuqua |
| 4,603,699 A | 8/1986 | Himpens |
| 4,696,288 A | 9/1987 | Kuzmak et al. |
| 4,760,837 A | 8/1988 | Petit |
| 4,858,619 A | 8/1989 | Toth |
| 4,872,483 A | 10/1989 | Shah |
| 4,881,939 A | 11/1989 | Newman |
| 4,919,650 A | 4/1990 | Feingold et al. |
| 4,989,756 A | 2/1991 | Kagamihara et al. |
| 5,074,868 A | 12/1991 | Kuzmak |
| 5,120,313 A | 6/1992 | Elftman |
| 5,160,338 A | 11/1992 | Vincent |
| 5,201,753 A | 4/1993 | Lampropoulos |
| 5,226,429 A | 7/1993 | Kuzmak |
| 5,259,399 A | 11/1993 | Brown |
| 5,277,333 A | 1/1994 | Shimano |
| 5,318,533 A | 6/1994 | Adams et al. |
| 5,383,858 A | 1/1995 | Reilly et al. |
| 5,425,716 A | 6/1995 | Kawasaki et al. |
| 5,449,368 A | 9/1995 | Kuzmak |
| 5,496,313 A | 3/1996 | Gentelia et al. |
| 5,569,839 A | 10/1996 | Ajot et al. |
| 5,601,604 A | 2/1997 | Vincent |
| 5,649,546 A | 7/1997 | Steinbeck |
| 5,658,298 A | 8/1997 | Vincent et al. |
| 5,681,284 A | 10/1997 | Hershowitz |
| 5,741,232 A | 4/1998 | Reilly et al. |
| 5,748,200 A | 5/1998 | Funahashi |
| 5,758,667 A | 6/1998 | Slettenmark |
| 5,795,333 A | 8/1998 | Reilly et al. |
| 5,808,203 A | 9/1998 | Nolan, Jr. et al. |
| RE36,176 E | 3/1999 | Kuzmak |
| 5,891,089 A | 4/1999 | Katz et al. |
| 5,910,149 A | 6/1999 | Kuzmak |
| 5,938,669 A | 8/1999 | Klaiber et al. |
| 5,997,502 A | 12/1999 | Reilly et al. |
| 6,010,511 A | 1/2000 | Murphy |
| 6,074,341 A | 6/2000 | Anderson et al. |
| 6,090,064 A | 7/2000 | Reilly et al. |
| 6,102,678 A | 8/2000 | Peclat |
| 6,102,922 A | 8/2000 | Jakobsson et al. |
| 6,117,086 A | 9/2000 | Shulze |
| 6,129,668 A | 10/2000 | Haynor et al. |
| 6,179,569 B1 | 1/2001 | Kojima et al. |
| 6,210,347 B1 | 4/2001 | Forsell |
| 6,221,024 B1 | 4/2001 | Miesel |
| 6,306,116 B1 | 10/2001 | Hancock |
| 6,371,942 B1 | 4/2002 | Schwartz et al. |
| 6,402,717 B1 | 6/2002 | Reilly et al. |
| 6,402,718 B1 | 6/2002 | Reilly et al. |
| 6,432,040 B1 | 8/2002 | Meah |
| 6,453,907 B1 | 9/2002 | Forsell |
| 6,454,699 B1 | 9/2002 | Forsell |
| 6,461,293 B1 | 10/2002 | Forsell |
| 6,464,628 B1 | 10/2002 | Forsell |
| 6,470,892 B1 | 10/2002 | Forsell |
| 6,475,136 B1 | 11/2002 | Forsell |
| 6,475,192 B1 | 11/2002 | Reilly et al. |
| 6,511,490 B2 | 1/2003 | Robert |
| 6,547,801 B1 | 4/2003 | Dargent et al. |
| 6,562,008 B1 | 5/2003 | Reilly et al. |
| 6,579,301 B1 | 6/2003 | Bales et al. |
| 6,635,020 B2 | 10/2003 | Tripp, Jr. et al. |
| 6,638,258 B2 | 10/2003 | Schwartz et al. |
| 6,676,674 B1 | 1/2004 | Dudai |
| 6,691,047 B1 | 2/2004 | Fredericks |
| 6,725,726 B1 | 4/2004 | Adolfs et al. |
| 6,733,478 B2 | 5/2004 | Reilly et al. |
| 6,778,927 B2 | 8/2004 | Cha et al. |
| 6,799,698 B2 | 10/2004 | Ono et al. |
| 6,808,513 B2 | 10/2004 | Reilly et al. |
| 6,966,875 B1 | 11/2005 | Longobardi |
| 7,027,935 B2 | 4/2006 | Shimase et al. |
| 7,037,344 B2 | 5/2006 | Kagan et al. |
| 7,044,933 B2 | 5/2006 | VanDiver et al. |
| 7,060,080 B2 | 6/2006 | Bachmann |
| 7,118,526 B2 | 10/2006 | Egle |
| 7,128,750 B1 | 10/2006 | Stergiopulos |
| 7,195,610 B1 | 3/2007 | Flachbart |
| 7,238,191 B2 | 7/2007 | Bachmann |
| 7,282,023 B2 | 10/2007 | Frering |
| 7,288,064 B2 | 10/2007 | Boustani et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,598 B2 | 1/2008 | Nishino |
| 7,338,433 B2 | 3/2008 | Coe |
| 7,351,198 B2 | 4/2008 | Byrum et al. |
| 7,364,542 B2 | 4/2008 | Jambor et al. |
| 7,367,937 B2 | 5/2008 | Jambor et al. |
| 7,416,528 B2 | 8/2008 | Crawford et al. |
| 7,481,763 B2 | 1/2009 | Hassler, Jr. et al. |
| 7,500,944 B2 | 3/2009 | Byrum et al. |
| 7,507,221 B2 | 3/2009 | Neer |
| 7,530,943 B2 | 5/2009 | Lechner |
| 7,585,280 B2 | 9/2009 | Wilson et al. |
| 7,594,885 B2 | 9/2009 | Byrum |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,699,770 B2 | 4/2010 | Hassler, Jr. et al. |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,927,270 B2 | 4/2011 | Dlugos et al. |
| 2001/0011543 A1 | 8/2001 | Forsell |
| 2002/0038105 A1 | 3/2002 | Schwartz et al. |
| 2002/0095181 A1 | 7/2002 | Beyar |
| 2002/0123716 A1 | 9/2002 | VanDiver et al. |
| 2002/0133081 A1 | 9/2002 | Ackerman et al. |
| 2002/0139208 A1 | 10/2002 | Yatskov |
| 2002/0152816 A1 | 10/2002 | Kim |
| 2002/0177811 A1 | 11/2002 | Reilly et al. |
| 2002/0198548 A1 | 12/2002 | Robert |
| 2003/0009123 A1 | 1/2003 | Brugger |
| 2003/0045775 A1 | 3/2003 | Forsell |
| 2003/0060754 A1 | 3/2003 | Reilly et al. |
| 2003/0073880 A1 | 4/2003 | Polsky et al. |
| 2003/0167022 A1 | 9/2003 | Dijkman |
| 2003/0171887 A1 | 9/2003 | Cha et al. |
| 2003/0208212 A1 | 11/2003 | Cigaina |
| 2003/0213285 A1 | 11/2003 | Wheeler et al. |
| 2004/0034479 A1 | 2/2004 | Shimase et al. |
| 2004/0069714 A1 | 4/2004 | Ferguson |
| 2004/0153106 A1 | 8/2004 | Dudai |
| 2004/0171942 A1 | 9/2004 | Ackerman et al. |
| 2004/0230137 A1 | 11/2004 | Mouton |
| 2004/0235025 A1 | 11/2004 | Mori et al. |
| 2004/0243057 A1 | 12/2004 | Vinten-Johansen |
| 2004/0254533 A1 | 12/2004 | Schriver et al. |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0070934 A1 | 3/2005 | Tanaka et al. |
| 2005/0070937 A1 | 3/2005 | Jambor et al. |
| 2005/0119672 A1 | 6/2005 | Benchetrit |
| 2005/0131383 A1 | 6/2005 | Chen et al. |

(56) References Cited

U.S. PATENT DOCUMENTS

| | | |
|---|---|---|
| 2005/0143765 A1 | 6/2005 | Bachmann et al. |
| 2005/0143766 A1 | 6/2005 | Bachmann et al. |
| 2005/0177111 A1 | 8/2005 | Ozeri et al. |
| 2005/0183730 A1 | 8/2005 | Byrum |
| 2005/0192531 A1 | 9/2005 | Birk |
| 2005/0192601 A1 | 9/2005 | Demarais |
| 2005/0240155 A1 | 10/2005 | Conlon |
| 2005/0240156 A1 | 10/2005 | Conlon |
| 2005/0250979 A1 | 11/2005 | Coe |
| 2005/0251181 A1 | 11/2005 | Bachmann |
| 2005/0251182 A1 | 11/2005 | Bachmann |
| 2005/0277899 A1 | 12/2005 | Conlon et al. |
| 2005/0283041 A1 | 12/2005 | Egle |
| 2006/0009697 A1 | 1/2006 | Banet et al. |
| 2006/0074439 A1 | 4/2006 | Garner et al. |
| 2006/0079766 A1 | 4/2006 | Neer et al. |
| 2006/0079767 A1 | 4/2006 | Gibbs et al. |
| 2006/0149161 A1 | 7/2006 | Wilson et al. |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0189888 A1 | 8/2006 | Hassler, Jr. |
| 2006/0199997 A1 | 9/2006 | Hassler, Jr. et al. |
| 2006/0211912 A1 | 9/2006 | Dlugos et al. |
| 2006/0235448 A1 | 10/2006 | Roslin et al. |
| 2006/0264762 A1 | 11/2006 | Starr |
| 2007/0001447 A1 | 1/2007 | Fennington, Jr. |
| 2007/0015954 A1 | 1/2007 | Dlugos |
| 2007/0015955 A1 | 1/2007 | Tsonton |
| 2007/0027356 A1 | 2/2007 | Ortiz |
| 2007/0106153 A1 | 5/2007 | Neer et al. |
| 2007/0156013 A1 | 7/2007 | Birk |
| 2007/0167672 A1 | 7/2007 | Dlugos et al. |
| 2007/0185462 A1 | 8/2007 | Byrum |
| 2007/0191717 A1 | 8/2007 | Rosen et al. |
| 2007/0218083 A1 | 9/2007 | Brooks |
| 2007/0235083 A1 | 10/2007 | Dlugos |
| 2007/0250085 A1 | 10/2007 | Bachmann et al. |
| 2007/0250086 A1 | 10/2007 | Wiley et al. |
| 2007/0255336 A1 | 11/2007 | Herbert et al. |
| 2007/0265645 A1 | 11/2007 | Birk et al. |
| 2008/0009680 A1 | 1/2008 | Hassler, Jr. |
| 2008/0015406 A1 | 1/2008 | Dlugos |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0108896 A1 | 5/2008 | Gibbs et al. |
| 2008/0108941 A1 | 5/2008 | Neer |
| 2008/0108943 A1 | 5/2008 | Wagner |
| 2008/0114302 A1 | 5/2008 | Neer |
| 2008/0221598 A1 | 9/2008 | Dlugos |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0294097 A1 | 11/2008 | Kim et al. |
| 2008/0306443 A1 | 12/2008 | Neer et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0163803 A1 | 6/2009 | Neer et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0188494 A1 | 7/2009 | Imai et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216193 A1 | 8/2009 | Schriver et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0241677 A1 | 10/2009 | Klees et al. |
| 2009/0270759 A1 | 10/2009 | Wilson et al. |
| 2009/0270904 A1 | 10/2009 | Birk et al. |
| 2009/0306462 A1 | 12/2009 | Lechner |
| 2009/0312635 A1 | 12/2009 | Shimchuk et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan et al. |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk et al. |
| 2011/0033073 A1 | 2/2011 | Inoshita |
| 2011/0130626 A1 | 6/2011 | Hassler, Jr. et al. |

FOREIGN PATENT DOCUMENTS

| | | |
|---|---|---|
| DE | 19802615 | 8/1999 |
| EP | 1396242 | 3/2004 |
| EP | 1396243 | 3/2004 |
| EP | 1547549 | 6/2005 |
| EP | 1600183 | 11/2005 |
| EP | 1602346 | 12/2005 |
| EP | 1704833 | 9/2006 |
| EP | 1736123 | 12/2006 |
| EP | 1949875 | 7/2008 |
| EP | 1967168 | 9/2008 |
| EP | 1992316 | 11/2008 |
| EP | 2095797 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 00/09047 | 2/2000 |
| WO | WO 00/15158 | 3/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 03/105732 | 12/2003 |
| WO | WO 2004/019671 | 3/2004 |
| WO | WO 2005/009305 | 2/2005 |
| WO | WO 2009/023247 | 2/2009 |

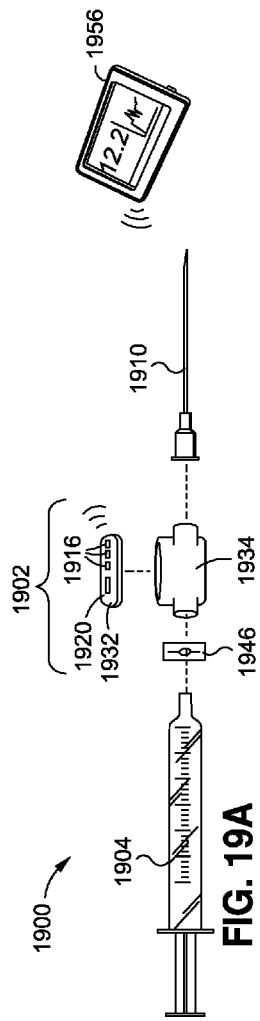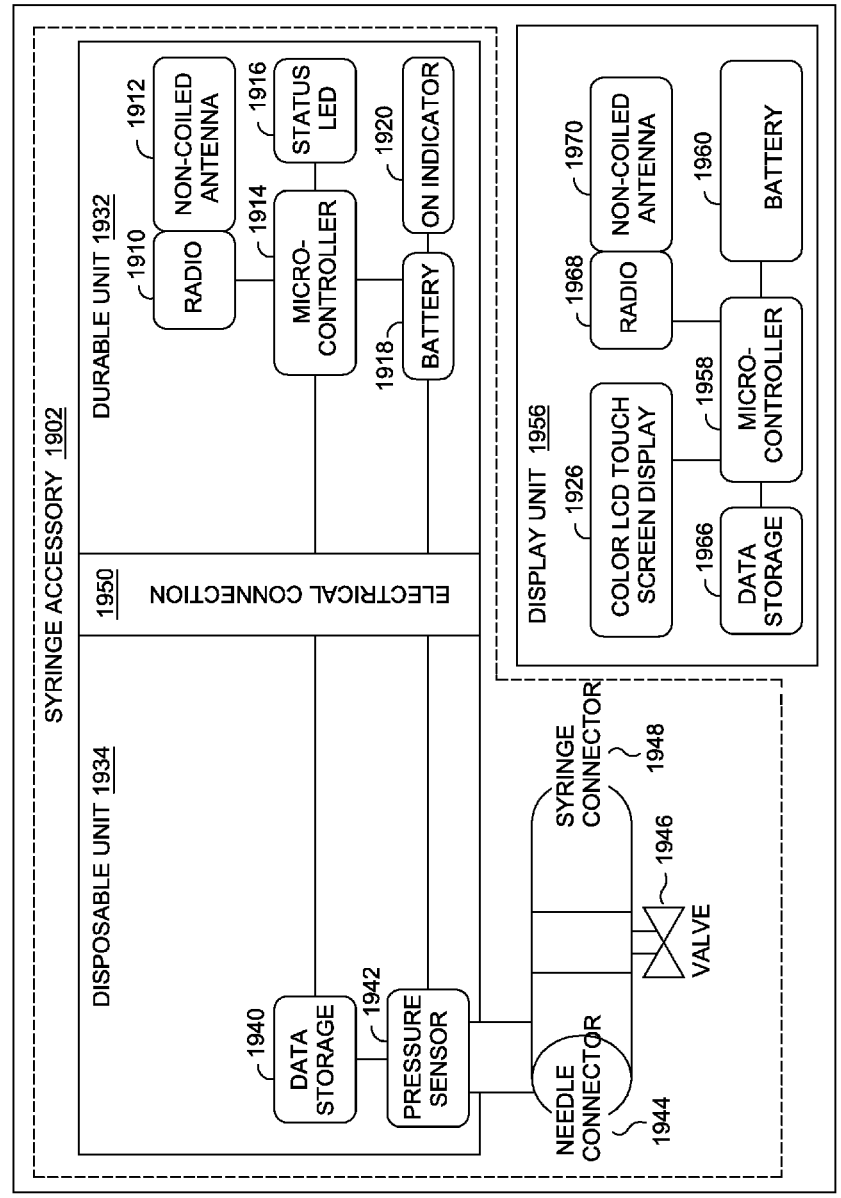
FIG. 19A
FIG. 19B

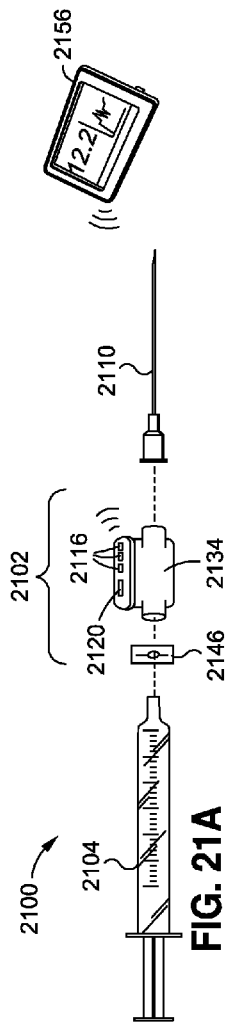
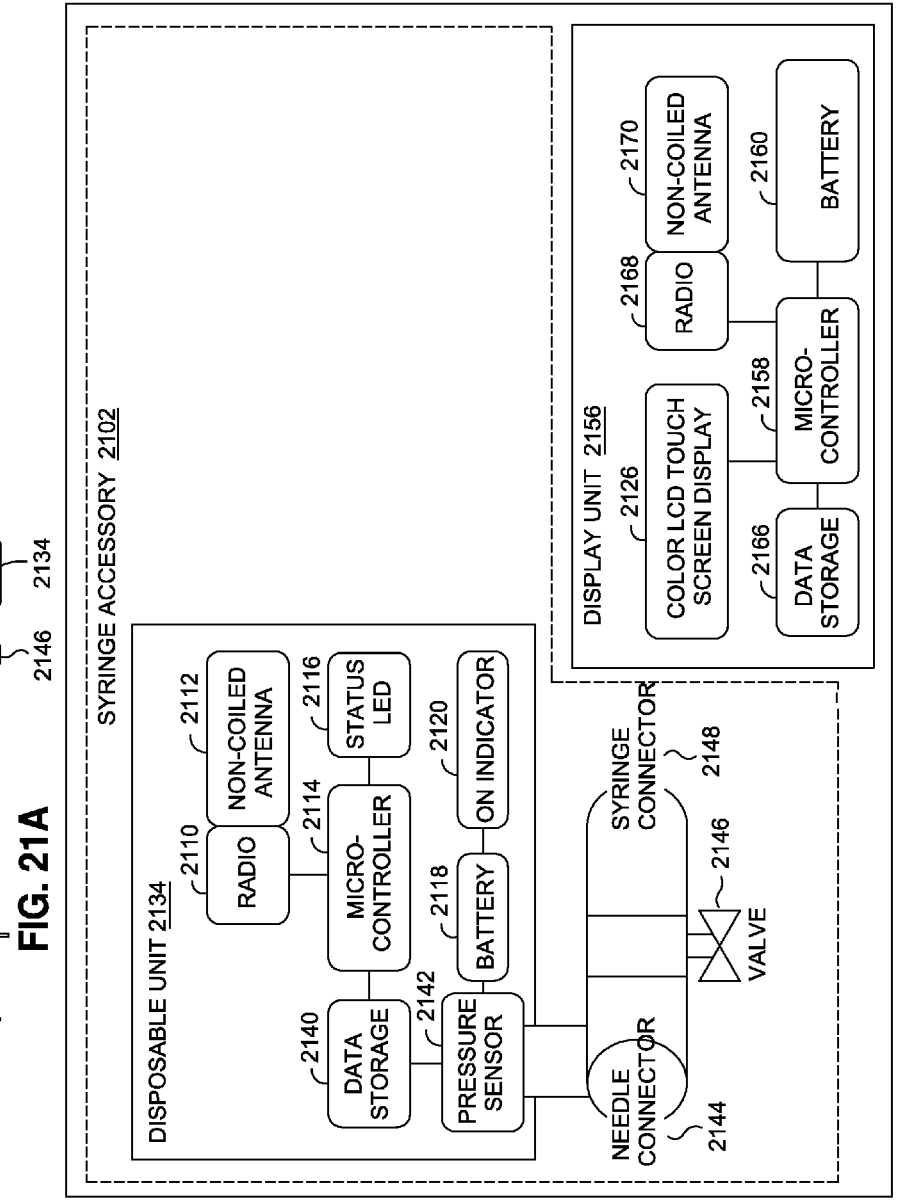
FIG. 21A
FIG. 21B

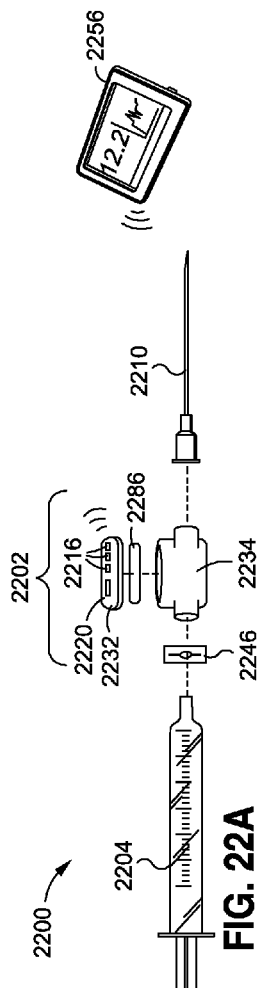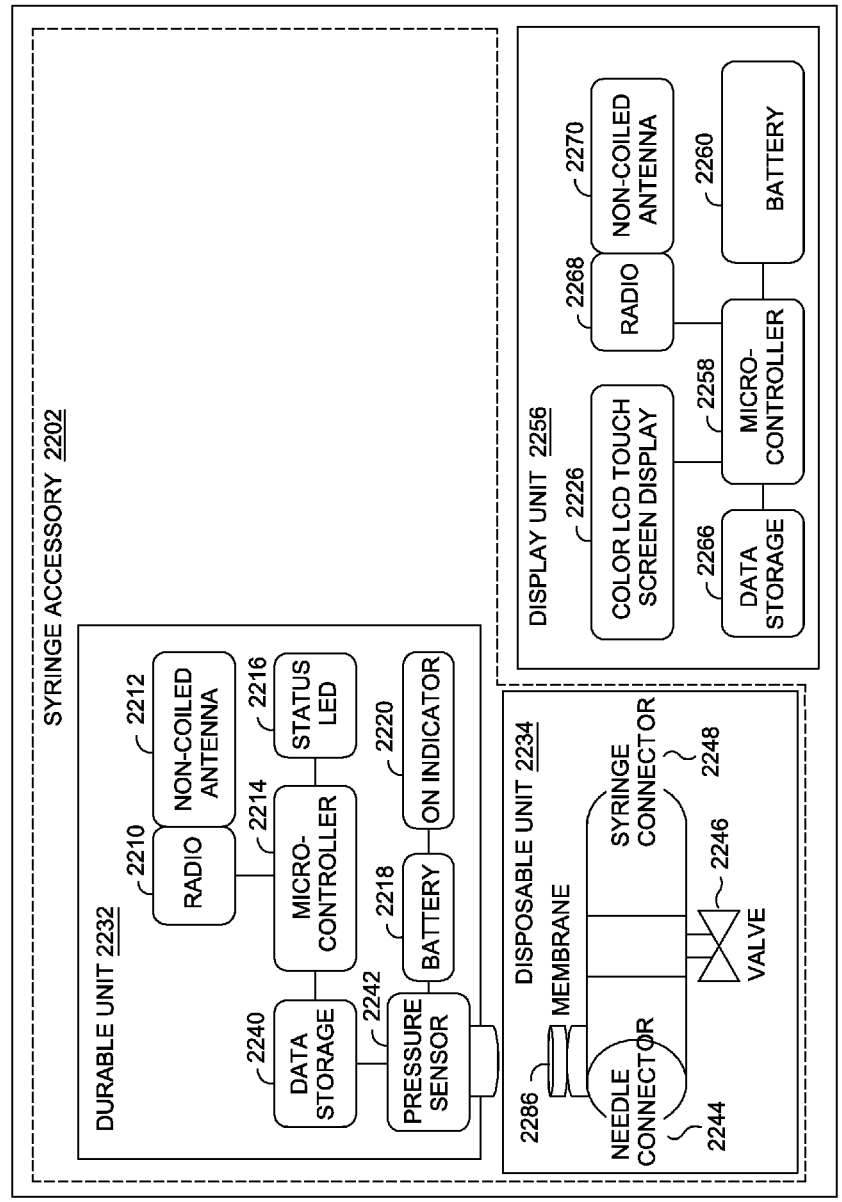

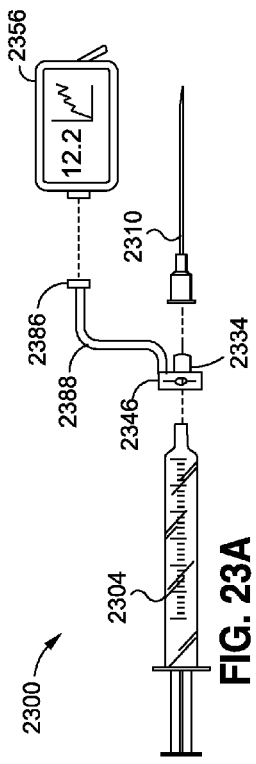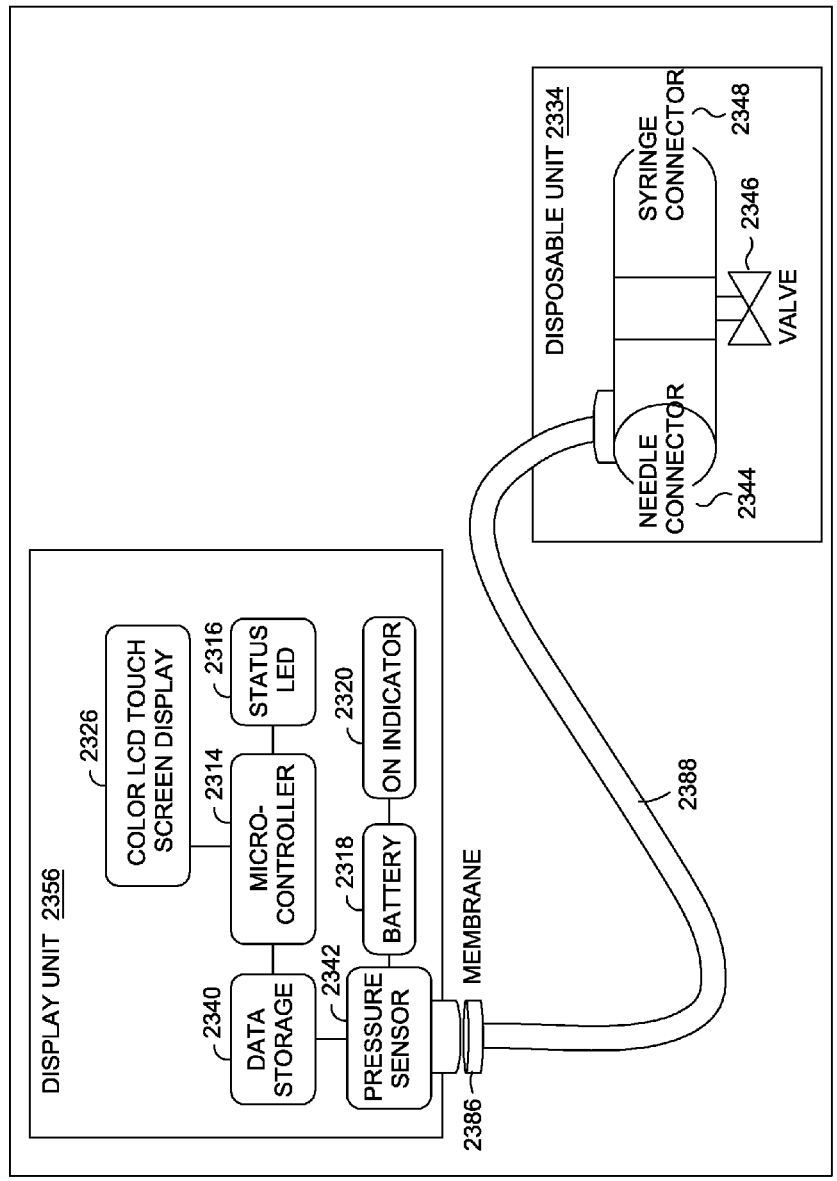

METHOD AND SYSTEM FOR DETERMINING THE PRESSURE OF A FLUID IN A SYRINGE, AN ACCESS PORT, A CATHETER, AND A GASTRIC BAND

CROSS REFERENCE TO RELATED APPLICATIONS

This application is a continuation-in-part of U.S. application Ser. No. 12/769,516, entitled "METHOD AND SYSTEM FOR DETERMINING THE PRESSURE OF A FLUID IN A SYRINGE, AN ACCESS PORT, A CATHETER, AND A GASTRIC BAND," filed on Apr. 28, 2010, the entire disclosure of which is incorporated herein by reference.

FIELD

The present invention generally relates to a method and system for determining pressure in a syringe, and more specifically to a syringe pressure accessory which can be connected to a syringe to determine the pressure of a fluid in a syringe, an access port, a catheter, and a gastric band.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the passage of food into a lower portion of the stomach. When the stoma is of an appropriate size that is restricted by a gastric band, food held in the upper portion of the stomach provides a feeling of satiety or fullness that discourages overeating. Unlike gastric bypass procedures, the gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

However, adjustment of the gastric band is conventionally performed by a syringe. The amount of fluid added by the syringe is often determined by a visual inspection of the syringe by the user. Such methods are often inaccurate since the user may not be able to determine accurately an amount of fluid injected into the gastric band through only a visual inspection of the syringe. Furthermore, the user may not know the precise pressure of the gastric band and thus may add too much or too little fluid to the gastric band. Detection of such pressure can be costly and time consuming since conventional pressure detection apparatuses will need to be sterilized after each use or disposed of after each use. Complete disposal of the pressure detection apparatus can be expensive and cost-prohibitive.

Some pressure detection apparatuses used in conjunction with syringes have also been disclosed, but these devices suffer from certain disadvantages. For example, Nolan, U.S. Pat. No. 5,808,203, generally discloses a pressure measuring device for a syringe, but Nolan integrates the pressure sensor as part of the syringe.

Reilly, U.S. Pat. No. 4,370,982, generally discloses an apparatus for measuring and detecting the pressure in a syringe being injected into a closed system. However, Reilly integrates the pressure sensor as part of the syringe.

Dlugos et al., U.S. Pat. Pub. No. 2008/0015406 generally discloses an external pressure sensing system. Dlugos discloses that a pressure sensing portion comprises a reusable sensor portion and a disposable cap portion. The reusable sensor portion and the disposable cap portion are configured to selectively engage one another. When coupled with the reusable sensor portion, the disposable cap portion is in fluid communication with the reusable sensor portion, such that pressure of fluid within tubing may be communicated to the reusable sensor portion via the disposable cap portion. In one embodiment, the disposable cap portion comprises the pressure dome described in Adolfs et al., U.S. Pat. No. 6,725,726. The reusable sensor portion comprises a pressure port, which is configured to receive such fluid pressure communications from the disposable cap portion. For instance, the pressure port may comprise a diaphragm or other structure suited for receiving fluid pressure communications. The reusable sensor portion further comprises a pressure sensor, such as a transducer, which is configured to provide pressure data via a cable to an interface component. The interface component is operable to process such pressure data and communicate it to a display device via a cable. However, Dlugos suffers from the drawback that it does not disclose the use of a disposable membrane, that the diaphragm is a reusable membrane, or that the diaphragm in the reusable sensor portion should contact a diaphragm in the disposable cap portion. This can, for example, result in inaccurate pressure information and/or contamination of the fluid being injected into the gastric band.

Thus, there is a need for a method and system for determining pressure in a syringe, and more specifically to a syringe pressure accessory which can be connected to a syringe to determine pressure in a syringe, an access port, a catheter, and a gastric band.

SUMMARY

The present invention is directed to a method and system for determining pressure in a syringe, and more specifically to a syringe pressure accessory which can be connected to a syringe to determine pressure in a syringe, an access port, a catheter, and a gastric band.

In one embodiment, the present invention is a syringe pressure accessory including a pressure sensor configured to be connected to a syringe and to detect pressure data corresponding to pressure in the syringe or the pressure of a fluid in the syringe, and a processor connected to the pressure sensor and to analyze the pressure data to determine the pressure in the syringe or the pressure of the fluid in the syringe.

In another embodiment, the present invention is a syringe pressure accessory including a pressure sensor configured to be connected to a syringe and to detect pressure data corresponding to pressure in the syringe, a processor connected to the pressure sensor and to analyze the pressure data to determine the pressure in the syringe, and an electrical parameter measuring system connected to the processor, the electrical parameter measuring system detecting electrical parameter data indicating a location of the syringe relative to a gastric band, or a port for a gastric band.

In another embodiment, the present invention is a syringe pressure accessory including a disposable unit configured to be connected to a syringe and including a pressure sensor detecting pressure data, and a durable unit configured to be connected to the disposable unit to determine the pressure in the syringe.

In another embodiment, the present invention is a syringe pressure accessory including a syringe attachment unit configured to be connected to a syringe and to detect pressure data of the syringe, and a first digital display unit configured to wirelessly connect to the syringe attachment unit, the first digital display unit configured to indicate a pressure corresponding to the pressure data of the syringe.

In another embodiment, the present invention is a method for determining pressure in multiple syringes including using a first disposable unit to detect pressure data of a first syringe, and using a durable unit to analyze the pressure data of the first syringe to determine the pressure in the first syringe.

In another embodiment, the present invention may comprise a syringe pressure accessory system include a syringe, a needle, a display unit and a syringe accessory, which may comprise a valve, a disposable unit and a durable unit. The syringe accessory may communicate with the display unit via the durable unit to provide the obtained pressure readings and other related information such that they may be displayed on the display unit.

In another embodiment, the present invention may comprise a syringe pressure accessory system which includes a syringe, a needle, a display unit and a syringe accessory, the latter of which may comprise a valve, a disposable unit and a durable unit. The disposable unit may include a battery and an "on" indicator. The syringe accessory may communicate with the display unit via the durable unit to provide the obtained pressure readings and other related information for display on the display unit.

In another embodiment, the present invention may comprise a syringe pressure accessory system include a syringe, a needle, a display unit and a syringe accessory, which may comprise a valve and a disposable unit. The disposable unit may include a microcontroller, a radio, an antenna, status LEDs, a pressure sensor, a battery, a data storage and an "on" indicator. The syringe accessory may communicate with the display unit via the disposable unit to provide the obtained pressure readings and other related information for display on the display unit.

In another embodiment, the present invention may comprise a syringe pressure accessory system which includes a syringe, a needle, a display unit and a syringe accessory, the latter of which may comprise a valve, a disposable unit and a durable unit. The durable unit may include a microcontroller, radio, antenna, status LEDs, a pressure sensor, a battery, a data storage and an "on" indicator. The disposable unit may include a membrane, a valve and needle/syringe connections. The syringe accessory may communicate with the display unit via the durable unit to provide the obtained pressure readings and other related information for display on the display unit.

In another embodiment, the present invention may comprise a syringe pressure accessory system which includes a syringe, a needle, a display unit and a disposable unit. The display unit may include a microcontroller, status LEDs, a pressure sensor, a battery, a data storage and an "on" indicator. The disposable unit may include a membrane, tubing, valve and needle/syringe connections. The display unit may obtain pressure readings via the pressure sensor and may display the obtained pressure readings and other related information.

In one embodiment, the present invention is a system for determining a pressure of a fluid in a gastric band for the treatment of obesity. The system may include a needle having a tip and a base, the needle further having a channel between the tip and the base for carrying the fluid. The system may also include a syringe fluidly coupled to the needle, the syringe having a plunger and a barrel. The system may also include a syringe pressure accessory having a first end coupled to the base of the needle and a second end coupled to the barrel of the syringe and providing a fluid path between the syringe and the needle. The syringe pressure accessory may include a disposable unit disposable after a single use, the disposable unit having a pressure sensor configured to access the fluid path for obtaining pressure data. The syringe pressure accessory may also include a durable unit configured to be reusable and coupled to the disposable unit. The durable unit is positioned at a location outside the fluid path and the durable unit is used for analyzing the obtained pressure data. The syringe pressure accessory may also include a valve located between the syringe and the needle, the valve having an open configuration for allowing the fluid to flow through the valve and a closed configuration for preventing the fluid from flowing through the valve which isolates the pressure of the fluid and improves the accuracy of the pressure data obtained by the pressure sensor.

BRIEF DESCRIPTION OF THE DRAWINGS

FIG. 19A illustrates a perspective, exploded view of a syringe pressure accessory system according to an embodiment of the present invention.

FIG. 19B illustrates a box diagram of the syringe pressure accessory system of FIG. 19A according to an embodiment of the present invention.

FIG. 21A illustrates a perspective, exploded view of a syringe pressure accessory system according to an embodiment of the present invention.

FIG. 21B illustrates a box diagram of the syringe pressure accessory system of FIG. 21A according to an embodiment of the present invention.

FIG. 22A illustrates a perspective, exploded view of a syringe pressure accessory system according to an embodiment of the present invention.

FIG. 22B illustrates a box diagram of the syringe pressure accessory system of FIG. 22A according to an embodiment of the present invention.

FIG. 23A illustrates a perspective, exploded view of a syringe pressure accessory system according to an embodiment of the present invention.

FIG. 23B illustrates a box diagram of the syringe pressure accessory system of FIG. 23A according to an embodiment of the present invention.

DETAILED DESCRIPTION

Figure 1:
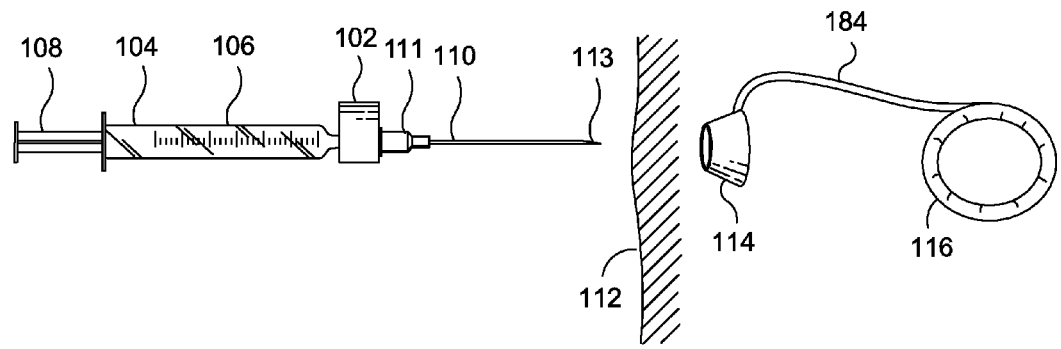
FIG. 1 illustrates syringe pressure accessory according to an embodiment of the present invention.

As seen in FIG. 1, in one embodiment, the present invention can include a syringe pressure accessory 102 attached to a syringe 104. The syringe 104 can include, for example, a barrel 106, a pump 108, and/or an optional needle 110. The syringe pressure accessory 102 can be attached, for example, to the barrel 106 and/or the needle 110. In one embodiment, the needle 110 may include a base 111 for attaching to the syringe 104 and a tip 113 for penetrating a patient's skin layer 112. The needle 110 may further include an internal channel 115 (see FIG. 7) exposed at the tip 113, the internal channel 115 extending from the base 111 to the tip 113 and configured to carry the fluid from the base 111 to the tip 113. Although the needle 110 is shown in FIG. 1, a tube, a catheter, or other connection device can be used instead of or in conjunction with the needle 110.

In FIG. 1, a gastric band 116 is connected to a port 114 by a tube 184. The port 114 can be, for example, an access port. The gastric band 116, the port 114, and/or the tube 184 are implanted within a patient and can lie beneath the skin layer 112. The syringe 104 can connect to the port 114 by piercing the skin layer 112 with the needle 110. The barrel 108 can be depressed to inject fluid into the port 114 and to the gastric band 116 or remove fluid from the port 114 and the gastric band 116.

Figure 2:
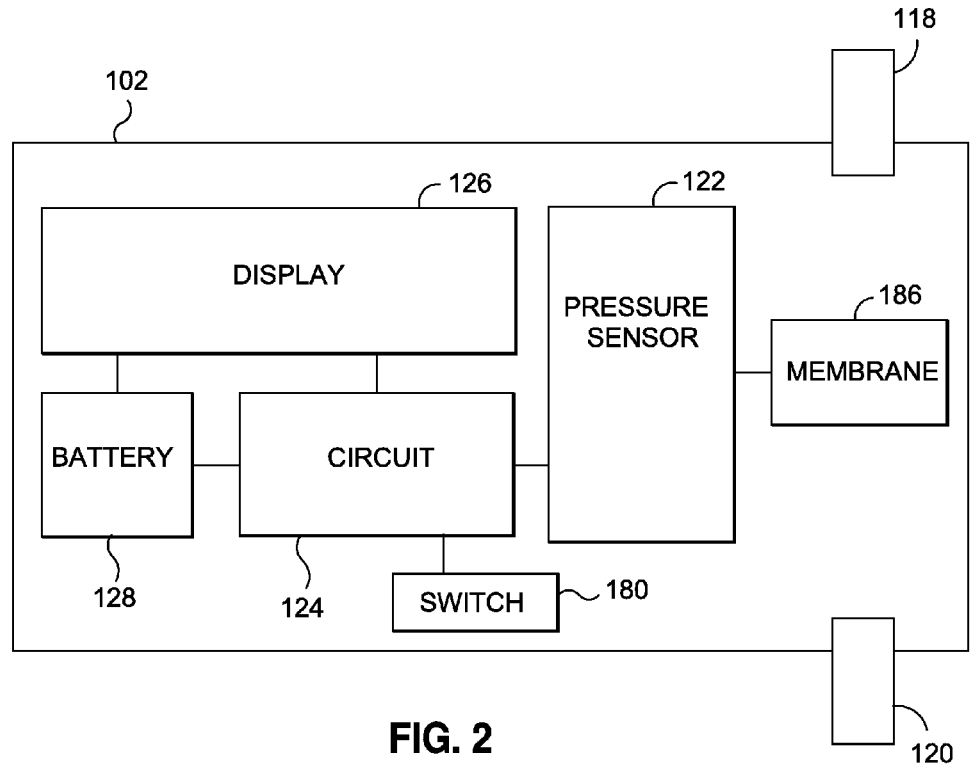
FIG. 2 illustrates a box diagram of a syringe pressure accessory according to an embodiment of the present invention.

One embodiment of the syringe pressure accessory 102 can be seen, for example, in FIG. 2. The syringe pressure accessory 102 can include, for example, a connection unit 118, a connection unit 120, a pressure sensor 122, a circuit 124, a display 126, a battery 128, a membrane 186, and/or a switch 180.

The syringe pressure accessory 102 can connect to the syringe 104 using the connection unit 118 and/or the connection unit 120. In one embodiment, the connection unit 118 can be a male connection or a female connection unit, and the connection unit 120 can be a male connection unit or a female connection unit. Furthermore, the barrel 106 can be connected to the syringe pressure accessory 102 at the connection unit 118 or the connection unit 120. In addition, the needle 110 can be connected to the connection unit 118 or the connection unit 120.

The membrane 186 can be connected to the pressure sensor 122. In one embodiment, the membrane 186 is in fluid connection with the syringe 104 and can be used, for example, to determine the pressure of the syringe 104. The membrane 186 can also be used, for example, to determine the pressure in the port 114, the gastric band 116, the needle 110, and/or a catheter connecting the syringe 104 to the port 114. The pressure in the syringe 104 can also correspond, for example, to the pressure in the port 114 and/or the gastric band 116.

The pressure sensor 122 can be connected, for example, to the membrane 186. The pressure sensor 122 can use the membrane 186 to detect pressure data. The pressure data can correspond, for example, to the pressure in the syringe 104. The pressure in the syringe 104 can correspond, for example, to the pressure in the port 114 and/or the gastric band 116.

The switch 180 is connected to the circuit 124 and can supply an on signal or an off signal to the circuit 124. The display 126 is connected to the circuit 124 and can display various pieces of information that are relevant to a user using the syringe pressure accessory 102. The battery 128 is connected, for example, to the display 126 and/or the circuit 124.

The battery 128 can store power and also supply power to the display 126, and/or the circuit 124. The battery 128 can also supply power to the pressure sensor 122 and/or any other electrical device in the syringe pressure accessory 102. In addition, the battery 128 can be, for example, rechargeable.

The circuit 124 can be connected, for example, to the switch 180, the pressure sensor 122, and/or the display 126. The circuit 124 can turn on or turn off the syringe pressure accessory 102 based on whether the circuit 124 receives an on signal or an off signal from the switch 180. The circuit 124 can also receive the pressure data from the pressure sensor 122, and analyze the pressure data to determine the pressure in the syringe 104 and/or the gastric band 116. In one embodiment, the circuit 124 can also control the display 126 to display the pressure of the syringe 104 and/or the gastric band 116. The circuit 124 can include, for example, a micro controller. The micro controller can be, for example, a processor.

Figure 3:
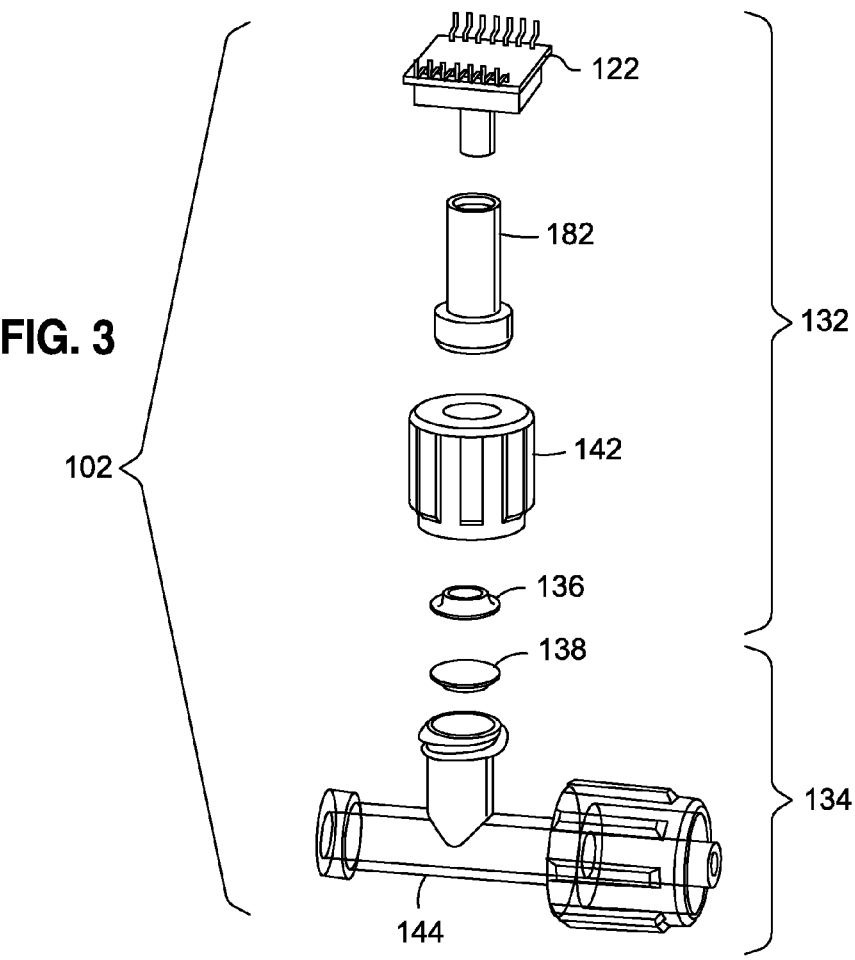
FIG. 3 illustrates a durable unit and a disposable unit for a syringe pressure accessory according to an embodiment of the present invention.

In one embodiment, the syringe pressure accessory 102 can include, for example, a durable unit 132 and a disposable unit 134, as seen in FIG. 3. The durable unit 132 can be connected, for example, to the disposable unit 134. The durable unit 132 can be reused while the disposable unit 134 can be disposed after each use. The disposable unit 134 can be disposed, for example, along with a syringe.

The durable unit 132 can include, for example, a pressure sensor 122, a flanged sleeve 182, a luer spin lock 142, and/or a reusable membrane 136. The luer spin lock 142 can be configured to secure the durable unit 132 to the disposable unit 134. The reusable membrane 136 can contact the disposable unit 134 and allow the pressure sensor 122 to detect pressure data from the disposable unit 134. The flanged sleeve 182 provides the pressure sensor 122 access to the reusable membrane 136. Although not shown in FIG. 3, the durable unit 132 can also include a processor to analyze the pressure data to determine the pressure in the syringe and/or the gastric band 116. Thus, the pressure sensor 122 can be, for example, a reusable pressure sensor.

The disposable unit 134 can include, for example, a t-connector 144, and/or a disposable membrane 138. The t-connector 144 can connect the disposable unit to a syringe and/or the durable unit 132. The t-connector 144 can also allow the disposable membrane 138 to be in fluid communication with the syringe and/or a gastric band.

In operation, the disposable membrane 138 can be in fluid communication with the syringe, an access port, a catheter, and/or a gastric band. The reusable membrane 136 can contact the disposable membrane 138 such that pressure in the syringe, the access port, the catheter, and/or the gastric band can be indicated and/or detected by the reusable membrane 136. The pressure sensor 122 can generate pressure data based on the pressure detected by the reusable membrane 136. Once the collection of the pressure data by the pressure sensor 122 is completed, the disposable unit 134 can be disposed along with the syringe. The process can then be repeated using another disposable unit 134 and another syringe, but with the same durable unit 132 for a new patient. Since the syringe is in fluid communication with the gastric band, the pressure of the syringe can be approximately equal to the pressure in the gastric band. Likewise, the pressure of the catheter and/or the access port can be approximately equal to the pressure in the gastric band. Thus, the pressure of the syringe, the catheter, and/or the access port can correspond, for example, to the pressure of the gastric band.

Figure 4:
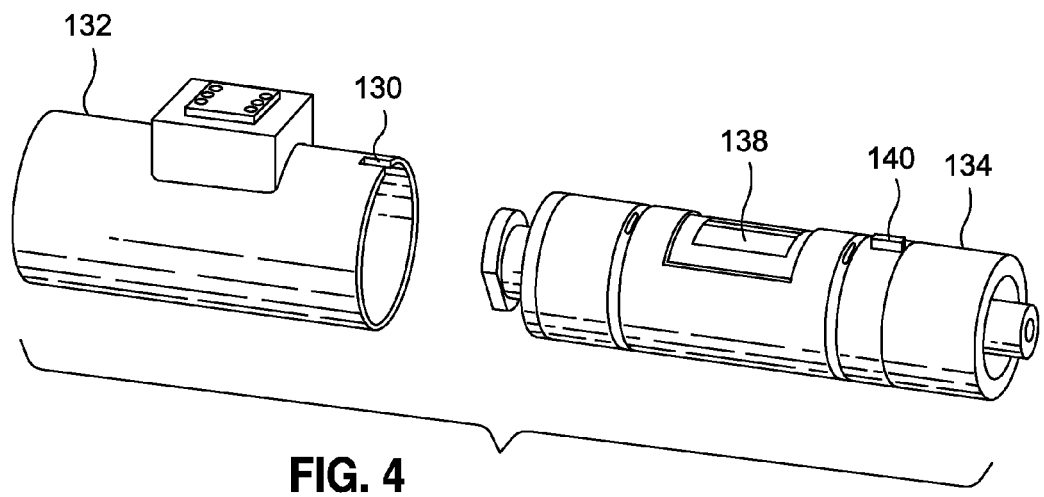
FIG. 4 illustrates a durable unit and a disposable unit according to an embodiment of the present invention.

FIG. 4 depicts another embodiment of the durable unit 132 and the disposable unit 134. As can be seen in FIG. 4, the disposable membrane 138 is exposed such that it can be in contact with the durable unit 132 to allow detection of the pressure within a syringe. The durable unit 132 includes a connection unit 130 which can be mated with a connection unit 140 to secure the durable unit 132 to the disposable unit 134. The connection unit 130 can be, for example, a notch, while the connection unit 140 can be, for example, a protrusion.

Figure 5:
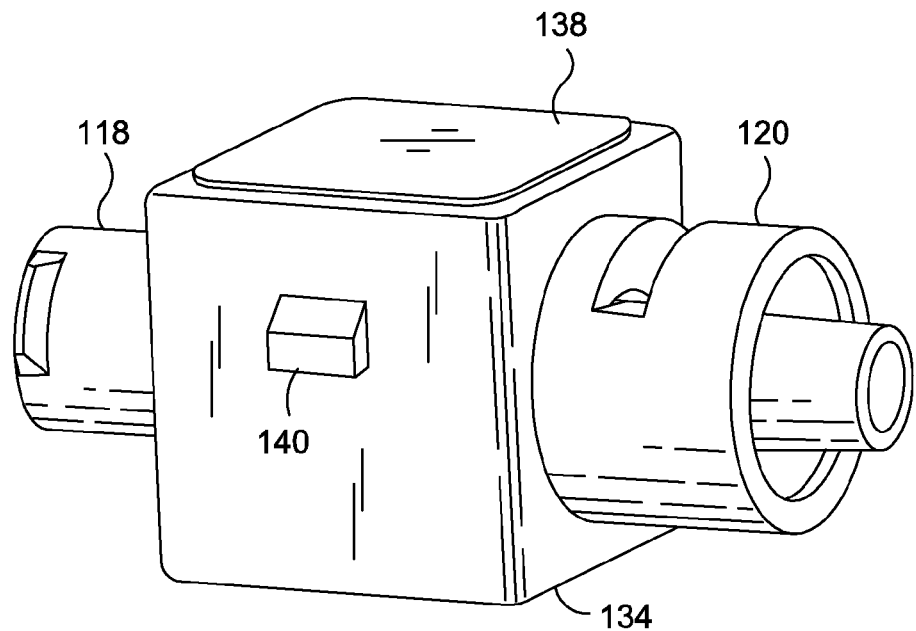
FIG. 5 illustrates a disposable unit according to an embodiment of the present invention.

FIG. 5 depicts another embodiment of the disposable unit 134. As can be seen, the disposable membrane 138 is exposed such that it can be in contact with the durable unit 132 (not shown) to allow detection of the pressure within a syringe. The connection unit 140 can be mated, for example, to a retention clip (not shown) in the durable unit 132. The connection unit 118 and the connection unit 120 can be used, for example, to connect the disposable unit 134 to a syringe.

Figure 6:
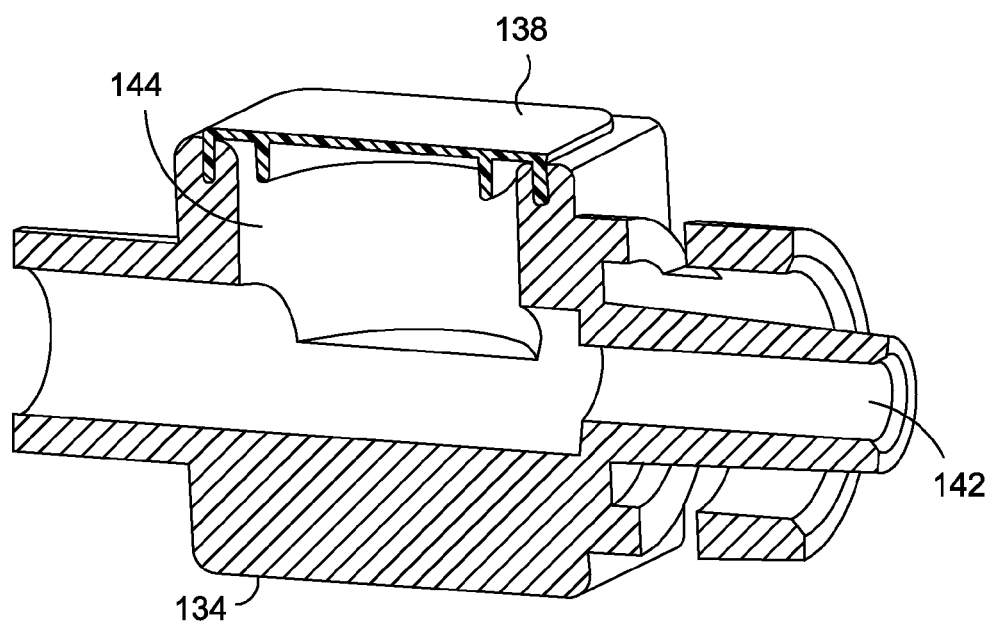
FIG. 6 illustrates a cross-section of a disposable unit according to an embodiment of the present invention.

FIG. 6 depicts a cross-section of the disposable unit 134 shown in FIG. 5. As can be seen, the disposable unit 134 includes a channel 142 and a chamber 144. The channel 142 can be in fluid communication with the syringe when the disposable unit 134 is connected to the syringe. The syringe can be in fluid communication with a gastric band. The channel 142 and the disposable membrane 138 are also in fluid connection with the chamber 144. Thus, when the disposable unit 134 is connected to the syringe, and the syringe is in fluid communication with the gastric band, the disposable membrane 138 can indicate a pressure of the syringe and/or the gastric band. The disposable unit 134 can also be in fluid communication with an access port and/or a catheter to indicate a pressure of the syringe and/or the gastric band.

Figure 7:
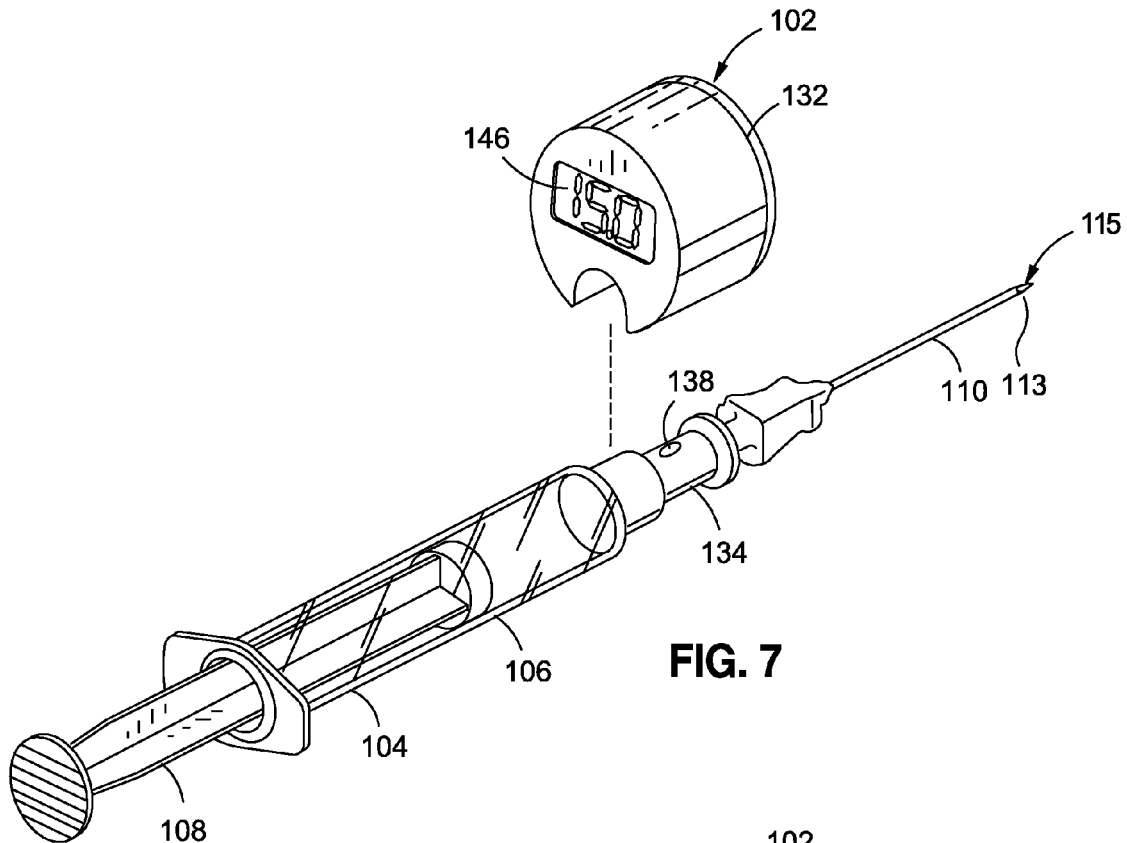
FIG. 7 illustrates a durable unit and a disposable unit according to an embodiment of the present invention.
Figure 8:
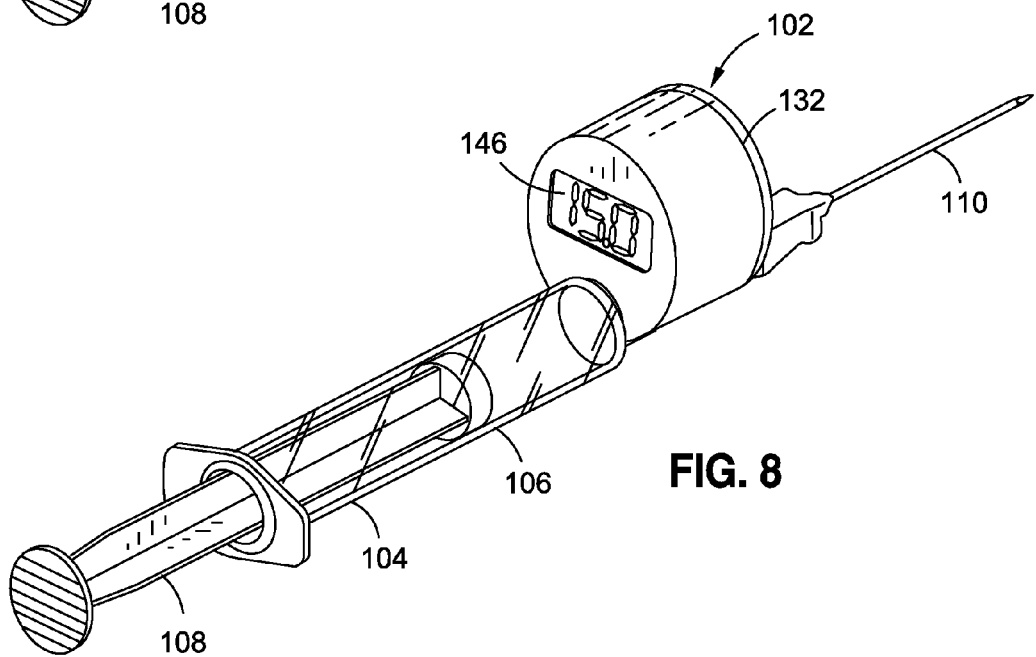
FIG. 8 illustrates a durable unit and a disposable unit according to an embodiment of the present invention.

FIG. 7 depicts another embodiment of the syringe pressure accessory 102 including the durable unit 132 and the disposable unit 134. As can be seen, the durable unit 132 includes, for example, a display 146. The display 146 can indicate, for example, the pressure of the syringe 104 and/or the gastric band 116. In one embodiment, the display 146 is a digital display. As can be seen, the disposable unit 134 is connected to the syringe 104. Furthermore, as seen in FIG. 7 and FIG. 8, the durable unit 132 can be connected to the disposable unit 134.

Figure 9:
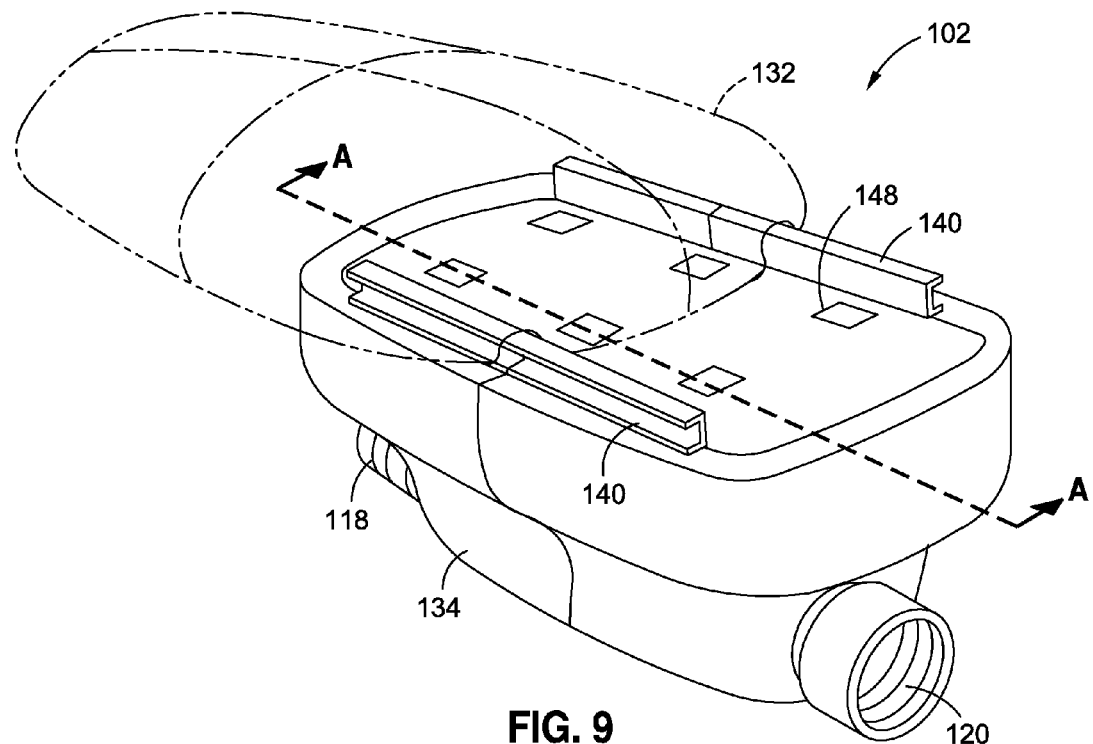
FIG. 9 illustrates a durable unit and a disposable unit according to an embodiment of the present invention.
Figure 10:
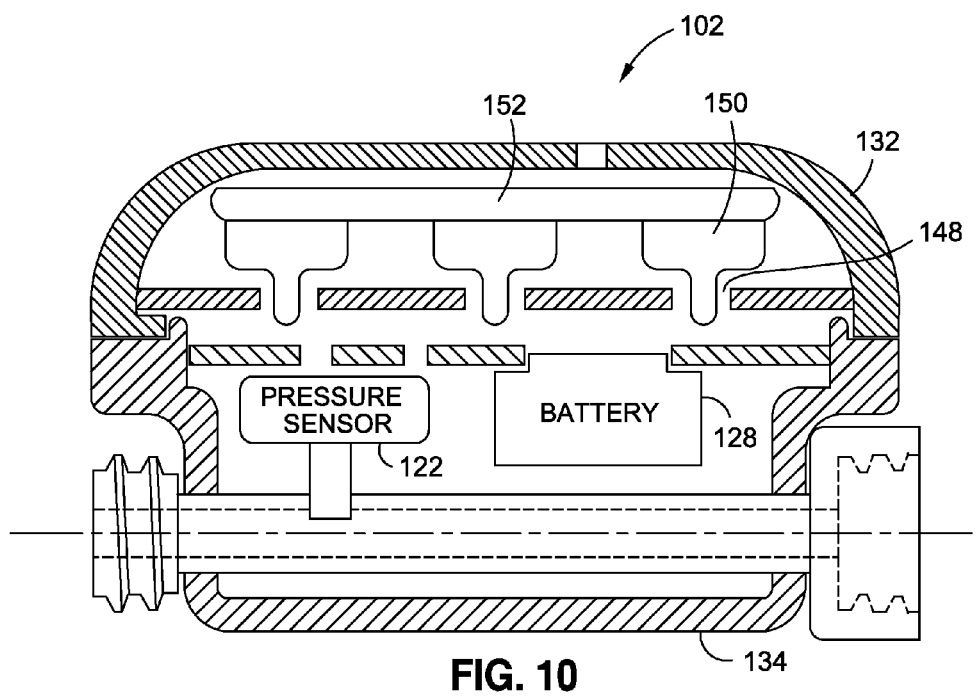
FIG. 10 illustrates a cross-section of a durable unit and a disposable unit according to an embodiment of the present invention.

FIG. 9 and FIG. 10 depict another embodiment of the syringe pressure accessory 102 including a durable unit 132 and a disposable unit 134. In FIG. 9 and FIG. 10, the pressure sensor 122 now resides in the disposable unit 134 instead of the durable unit 132. The pressure sensor 122 can be powered, for example, by the battery 128. The battery 128 can contain sufficient power, for example, to power the pressure sensor 122 before the pressure sensor 122 and the battery 128 are disposed of. The location of the pressure sensor 122 can obviate the need for a membrane, and thus the durable unit 132 and the disposable unit 134 can be constructed without a membrane. Thus, the syringe pressure accessory 102 can utilize a pressure sensor 122 in the disposable unit 134 that is disposable. The pressure sensor 122 can directly determine pressure data from the syringe.

A processor 152, however, may still reside in the durable unit 132. Furthermore, the disposable unit 134 can include metal contacts 148 and the durable unit 132 can include metal contacts 150. The metal contacts 148 and the metal contacts 150 are configured to mate with each other allowing the transfer of pressure data from the pressure sensor 122 in the disposable unit 134 to the processor 152 in the durable unit 132. In addition, as seen in FIG. 9, the connection unit 140 can be utilized to secure the durable unit 132 to the disposable unit 134.

Figure 11:
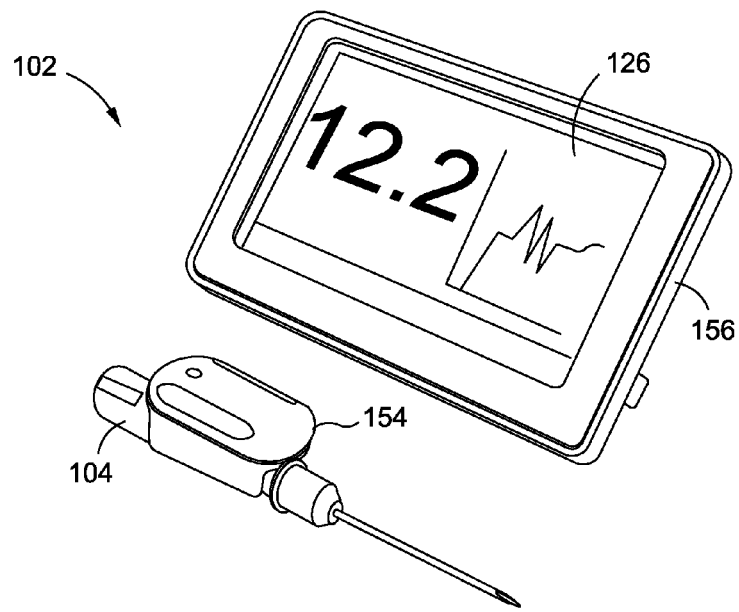
FIG. 11 illustrates a syringe pressure attachment unit and a display unit according to an embodiment of the present invention.

FIG. 11 depicts another embodiment of the syringe pressure accessory 102. In FIG. 11, the syringe pressure accessory 102 can include, for example, a syringe attachment unit 154 and a display unit 156. The display unit 156 can also be, for example, a receiver unit. The syringe attachment unit 154 can be attached to the syringe 104 and determine pressure data corresponding to the pressure within the syringe 104 and/or a gastric band. The syringe attachment unit 154 can wirelessly transmit the pressure data to the display unit 156. The display unit 156 can include, for example, a display 126. The display unit 156 can receive the pressure data and display information regarding the pressure data, such as a numerical representation of the pressure data or a pressure chart on the display 126.

Figure 12:
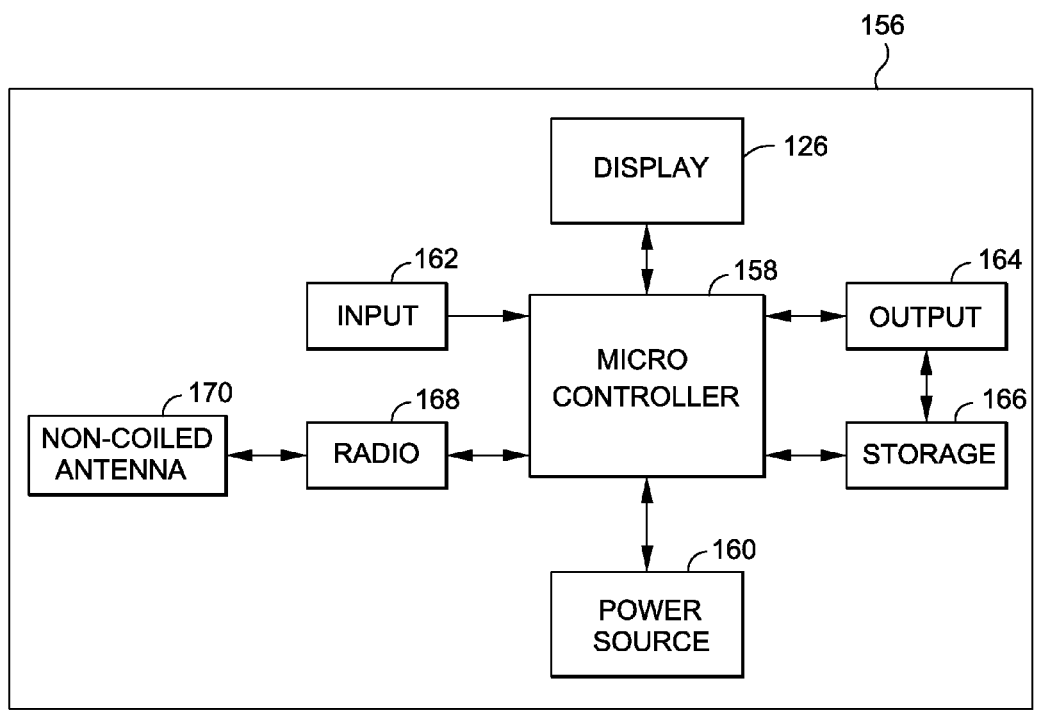
FIG. 12 illustrates a box diagram of a display/receiver unit according to an embodiment of the present invention.

FIG. 12 depicts an embodiment of the display unit 156. As seen in FIG. 12, the display unit 156 includes a display 126, a micro controller 158, a power source 160, an input 162, an output 164, a storage device 166, a radio 168, and/or a non-coiled antenna 170.

The display 126 is connected to the micro controller 158 and can display, for example, information related to the pressure of the syringe and/or the gastric band. The input 162 is connected, for example, to the micro controller 158. The input 162 can be, for example, a button, a mouse, a keyboard, a tilt sensor, a light sensor, a touch sensor, a security feature, and/or any other type of device which can supply information or data to the micro controller 158.

The output 164 can be connected, for example, to the micro controller 158 and/or the storage device 166. The output 164 can allow, for example, the output of data such as pressure data and/or pressure charts. In one embodiment, the output 164 can transmit the pressure data and/or the pressure charts to the storage 166 for storage.

The storage device 166 is connected to the micro controller 158 and/or the output 164. The storage device 166 can store, for example, the pressure data and/or the pressure charts. The storage can be, for example, a flash memory and/or a hard drive.

The power source 160 is connected to the micro controller 158. The power source 160 can be, for example, a battery, and/or a medical or a non-medical grade power supply. The power source can supply power to the micro controller 158 and/or any other electrical device in the syringe pressure accessory.

The radio 168 is connected, for example, to the micro controller 158 and/or the non-coiled antenna 170. The radio allows for wireless transmission and/or reception of data, such as the pressure data.

The non-coiled antenna 170 is connected, for example, to the radio 168. The non-coiled antenna 170 aids in the wireless transmission and/or reception of data, such as the pressure data. The non-coiled antenna can be, for example, easier and more cost-effective to implement than a coiled antenna.

The micro controller 158 is connected, for example, to the display 126, the input 162, the output 164, the storage 166, the power source 160, and/or the radio 168. The micro controller 158 can receive, for example, the pressure data from the input 162 and/or the radio 168. The micro controller 158 can analyze the pressure data to generate the pressure charts. The micro controller 158 can also output the pressure data and/or the pressure charts to the output 164 and/or the storage 166. In addition, the micro controller 158 can instruct the display 126 to display the pressure data and/or the pressure charts.

Figure 13:
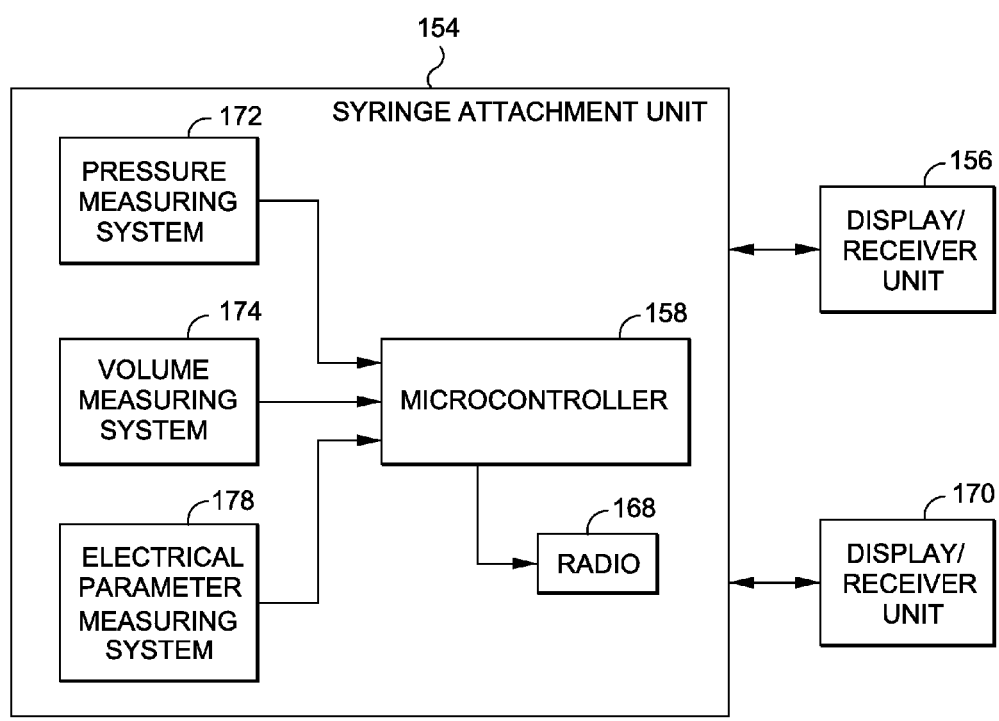
FIG. 13 illustrates a box diagram of a syringe pressure accessory unit according to an embodiment of the present invention.

Another embodiment of the syringe pressure accessory 102 can be seen, for example, in FIG. 13. As seen in FIG. 13, the syringe pressure accessory 102 includes a syringe attachment unit 154, a display unit 156, and a display unit 170. The display unit 156 and the display unit 170 can also be, for example, receiver units. As seen in FIG. 13, multiple display units are used. The syringe attachment unit 154 can be connected, for example, to a syringe. The syringe can be in fluid communication with an access port, a catheter, and/or a gastric band.

The syringe attachment unit 154 can be configured to exchange data with the display unit 156 and/or the display unit 170. The syringe attachment unit 154 can include, for example, a radio 168, a pressure measuring system 172, a volume measuring system 174, and/or an electrical parameter measuring system 178.

The radio 168 can be connected, for example, to the micro controller 158. The radio 168 can facilitate, for example, wireless communications between the micro controller 158 and the display unit 156 and/or the display unit 170.

The pressure measuring system 172 is connected, for example, to the micro controller 158. The pressure measuring system 172 can detect, for example, pressure data corresponding to a pressure of the syringe. The pressure of the syringe can correspond, for example, to the pressure of the gastric band.

The volume measuring system 174 is connected, for example, to the micro controller 158. The volume measuring system 174 can detect, for example, volume data indicating a volume of fluid dispensed by the syringe. The volume of fluid dispensed by the syringe can correlate, for example, with the volume of fluid received by the gastric band from the syringe. The volume measuring system 174 can be, for example, a differential pressure sensor, a Coriolis effect sensor, a paddle wheel, an optical sensor, and/or any other type of sensor that can detect volume of a fluid.

The electrical parameter measuring system 178 is connected, for example, to the micro controller 158. The electrical parameter measuring system 178 can detect, for example, electrical parameter data indicating a location of the syringe relative to a gastric band, or a port for a gastric band. The electrical parameter measuring system 178 can be, for example, an electrical sensor. The electrical parameter measuring system 178 can measure conductivity, resistance, breakdown voltage, and/or other electromagnetic properties over a range of frequencies, waveform shapes, voltage levels, and current levels. Such information can be used, for example, to determine a location of the needle of the syringe relative to the body tissue, determine the position of the needle of the syringe relative to the port, determine the status of the port, determine the health of the tissue, determine the tissue layer composition and depth, determine the status of the fluid in the port. The status of the port can include, for example, level of tissue ingrowths or encapsulation. The status of the fluid in the port can include, for example, an amount of bacterial growth and/or the pH level of fluids in the port.

The micro controller 158 can transmit, for example, the pressure data, the volume data, and/or the electrical parameter data to the display unit 156 and/or the display unit 170. The micro controller 158 can also analyze the pressure data, the volume data, and/or the electrical parameter data to generate various charts or images which can also be transmitted to the display unit 156, and/or the display unit 170. The display unit 156 and/or the display unit 170 can display some or all of the pressure data, the volume data, the electrical parameter data, and/or the various charts or images.

In one embodiment, the display unit 156 is configured to be used, for example, by a doctor or caretaker, while the display unit 170 is configured to be used, for example, by a patient. The display unit 156 can be more sophisticated and allow the display of a greater amount of information. The display unit 170 can be less sophisticated and allow the display of a reduced amount of information. Furthermore, in one embodiment, the display unit 156 can control the display of information on the display unit 170.

Figure 14:
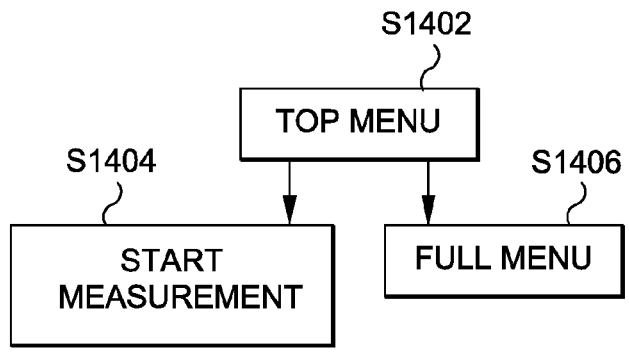
FIG. 14 illustrates a process according to an embodiment of the present invention.
Figure 15:
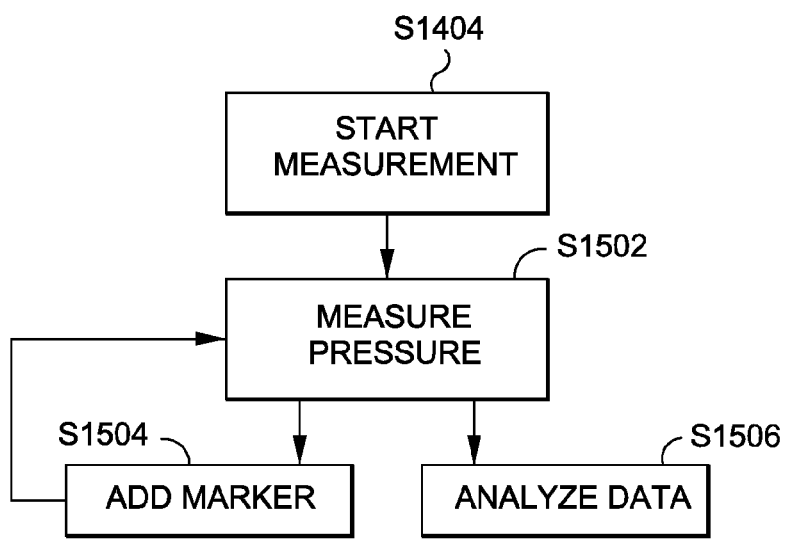
FIG. 15 illustrates a process according to an embodiment of the present invention.
Figure 16:
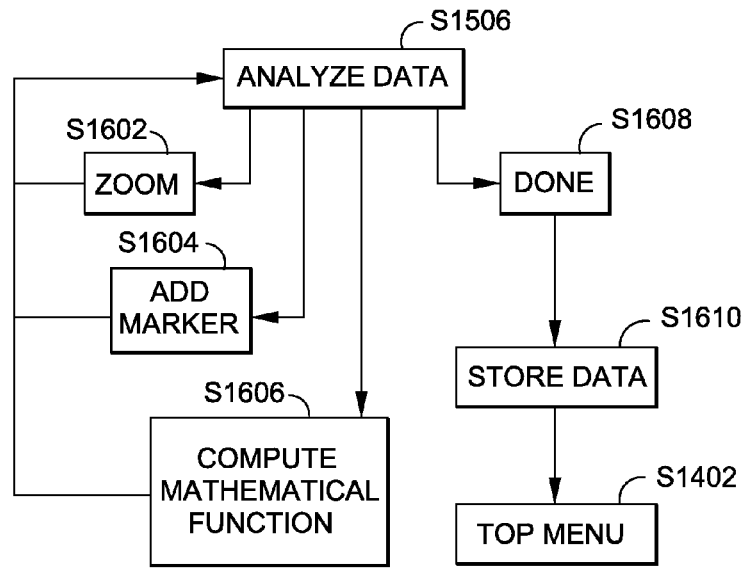
FIG. 16 illustrates a process according to an embodiment of the present invention.
Figure 17:
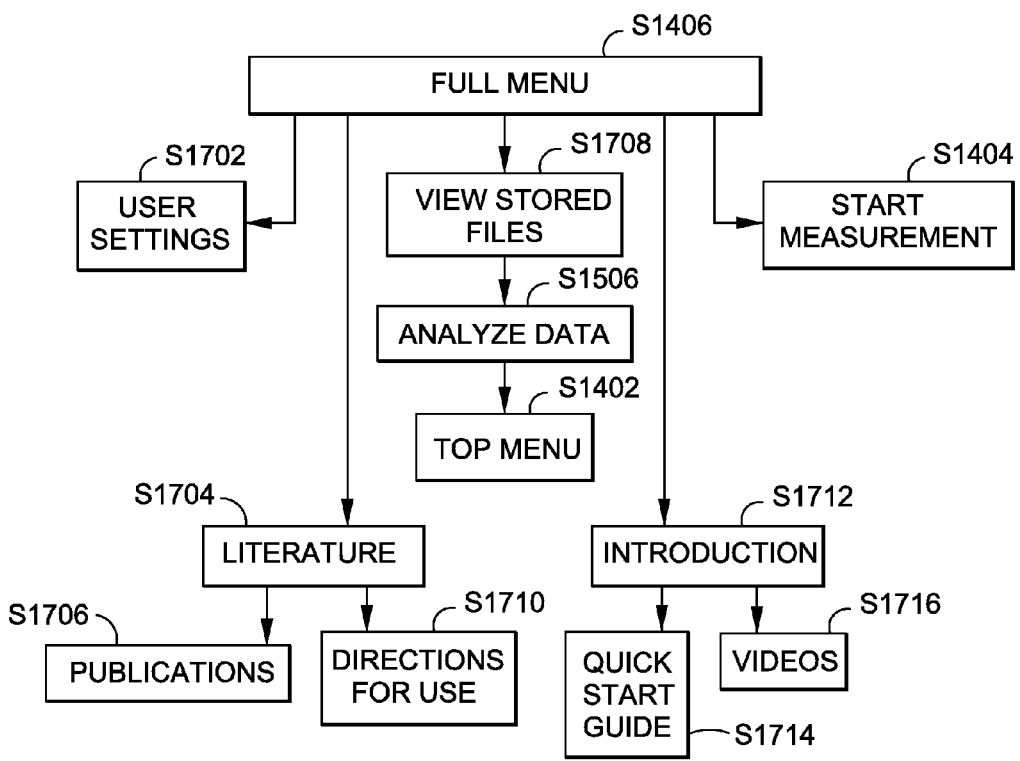
FIG. 17 illustrates a process according to an embodiment of the present invention.

In one embodiment, a syringe pressure accessory including, for example, the display unit 156 and/or the syringe attachment unit 154 can perform a process such as those depicted in FIG. 14, FIG. 15, FIG. 16, and/or FIG. 17. In Step S1402, a top menu can be displayed. For example, the micro controller 158 can instruct the display 126 to display a top menu including a start measurement button and a full menu button. If the start measurement button is pressed, the process proceeds to Step S1404. Otherwise, the process proceeds to Step S1406. In Step S1404, the start measurement process begins as shown in FIG. 15.

In Step S1502, pressure is measured. For example, the pressure measuring system 172 can measure medical data such as pressure data, volume data, and/or electrical parameter data, which are transmitted to the display unit 156. The display unit 156 can display the medical data and/or a medical chart from the medical data. Furthermore, the display unit 156 can display, for example, a marker button and an analyze data button. If the marker button is selected, the process proceeds to Step S1504. In Step S1504, a marker is added. For example, the display 126 can display a marker on the medical chart. The marker can indicate, for example an event. The marker can be, for example, a line, a rectangle, a triangle, a circle, or any other icon that can indicate an event. The process then repeats at Step S1502.

If the analyze data button is selected, the process proceeds to Step S1506. In Step S1506, the analyze data process begins as shown in FIG. 16. For example, the display 126 can display a zoom button, an add market button, a computer mathematical function button, and/or a done button. If the zoom button is selected, the process proceeds to Step S1602. In Step S1602, a zoom function is implemented. For example, the medical chart can be zoomed in. The process then repeats at Step S1506.

If the add marker button is selected, the process proceeds to Step S1604. In step S1604, a marker is added. The marker can indicate, for example an event. The marker can be, for example, a line, a rectangle, a triangle, a circle, or any other icon that can indicate an event. The process then repeats at Step S1506.

If the compute mathematical function button is selected, the process proceeds to Step S1606. In Step S1606, mathematical functions are computed. For example, data analysis can be performed on the medical data and the results of the data analysis can be displayed. Such analysis can include, for example, trends, valleys, peaks, recommendations, or any other type of analysis which may be beneficial to a doctor, caretaker, or patient.

If the done button is selected, the process proceeds to Step S1608. In Step S1608, the process prepares for the completion of the analyze data process. In Step S1610, data is stored. For example, the micro controller 158 can store the medical data. Alternatively the medical data can be transmitted to an external computer for storage. The process then repeats at Step S1402 (FIG. 14).

If the full menu button is selected in FIG. 14, the process proceeds to the full menu process in Step S1406, as shown in FIG. 16. In Step S1406 a full menu is displayed. The full menu can include, for example, a user settings button, a literature button, a view stored files button, an introduction button, and/or a start measurement button. If the user settings button is selected, the process proceeds to Step S1702. In Step S1702 user settings are displayed. For example, the user settings can allow the user to set touch sensitivity of the display 126, a brightness or contrast of the display 126, a layout of the display 126, or any other customizable feature for the display unit 156 and/or the syringe attachment unit 154. The process then repeats at Step S1406.

If the literature button is selected, the process proceeds to Step S1704. In Step S1704, literature options are displayed. For example, literature options such as a publications button and/or directions for use button can be displayed on the display 126. If the publications button is selected, the process proceeds to Step S1706.

In Step S1706, publications are displayed. For example, publications which may be helpful to the user may be displayed in the display 126. In addition, the user may select which publication to display. If the directions for use button is selected, the process proceeds to Step S1710. In Step S1710, the directions for use are displayed. For example, the display 126 can display the directions for using the syringe pressure accessory 102, the display unit 156, and/or the syringe attachment unit 154.

If the view stored files button is selected, the process proceeds to Step S1708. In Step S1708, the stored files are displayed. For example, medical data which are stored can be displayed in the display 126. The process then proceeds to Step S1506. In Step S1506, the data can be analyzed, as previously discussed above, and shown in FIG. 16. The process then proceeds to Step S1402. In Step S1402, the top menu is displayed as previously discussed above, and shown in FIG. 14.

If the introduction button is selected, the process proceeds to Step S1712. In Step S1712, an introduction is displayed. For example, a quick start guide button and/or a videos button can be displayed. If the quick start guide button is selected, the process proceeds to Step S1714.

In Step S1714, a quick start guide is displayed. For example, the display 126 can display a quick start guide for using the syringe pressure accessory 102, the display unit 156, and/or the syringe attachment unit 154. If the videos button is selected, the process proceeds to Step S1716. In Step S1716, videos are displayed. For example, videos can be displayed on the display 126 for using the syringe pressure accessory 102, the display unit 156, and/or the syringe attachment unit 154. However, other videos many also be displayed.

If the Start measurement button is selected, the process proceeds to Step S1404 as described above, and shown, for example, in FIG. 15.

Figure 18:
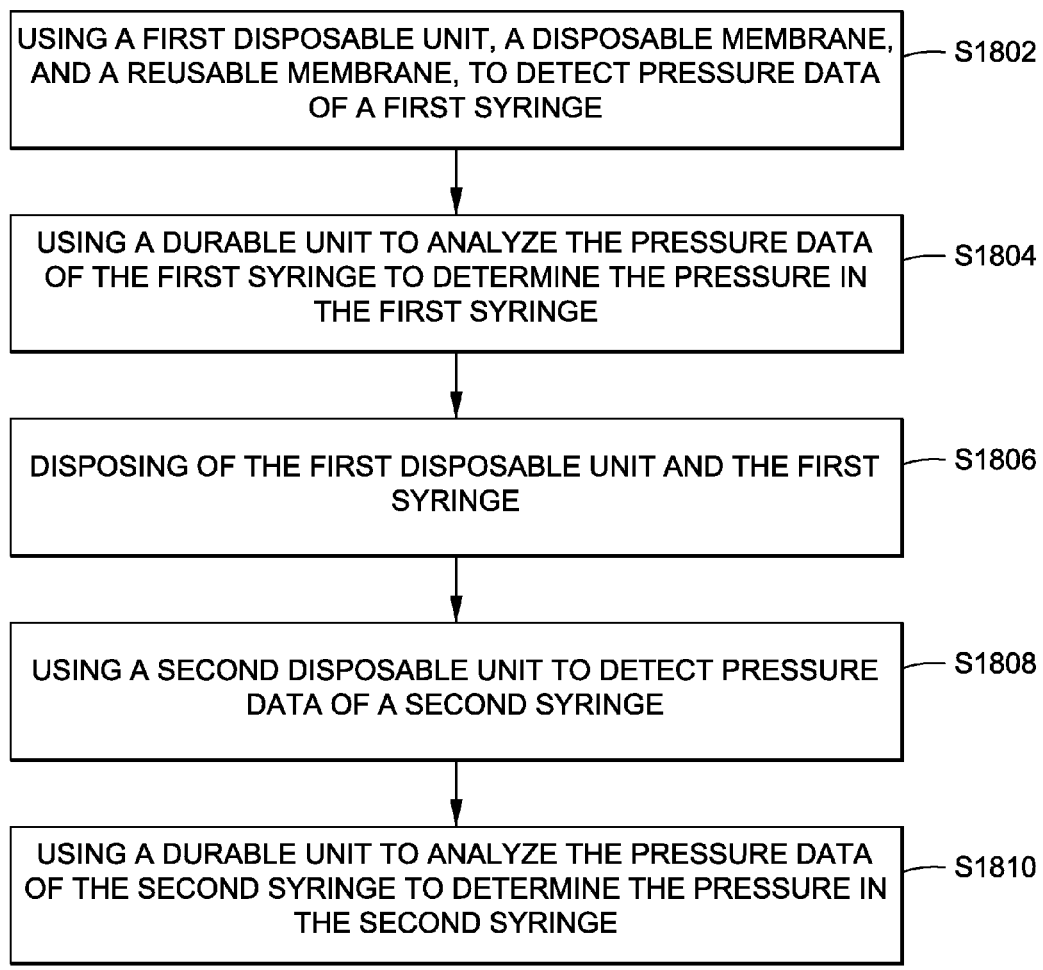
FIG. 18 illustrates a process according to an embodiment of the present invention.

In one embodiment, the present invention is a process as shown in FIG. 18. In Step S1802, a first disposable unit, a disposable membrane, and a reusable membrane are used to detect pressure data of a first syringe. For example, as shown in FIG. 3, the disposable unit 134, the disposable membrane 138, and a reusable membrane 136 can be used to detect pressure data of a syringe. In one embodiment, instead of using the disposable membrane 138 or the reusable membrane 136, only a disposable pressure sensor 122 is used.

In Step S1804, a durable unit can be used to analyze the pressure data of the first syringe to determine the pressure in the first syringe. For example, the durable unit 132 can be used to analyze the pressure data of the syringe to determine the pressure in the syringe.

In Step S1806, the first disposable unit and the first syringe can be disposed. For example, the disposable unit 134 and the syringe can be disposed. In Step S1808, a second disposable unit is used to detect pressure data of a second syringe. For example, another disposable unit 134 is used to detect the pressure data of a new syringe, aside from the disposable unit 134 and the syringe that were disposed. In Step S1810, a durable unit is used to analyze the pressure data of the second syringe to determine the pressure in the second syringe. For example, the same durable unit 132 is used to analyze the pressure data of the new syringe to determine the pressure in the new syringe.

FIGS. 19A-B, 20A-B, 21A-B, 22A-B and 23A-B illustrate additional embodiments of the present invention. As there may be a number of different ways to partition components based on cost, size and performance trade-offs, the following description of different embodiments are merely examples and should not be construed as limiting.

Turning to FIG. 19A, a syringe pressure accessory system 1900 is illustrated in an exploded view. As with certain other embodiments described herein, the syringe pressure accessory system 1900 may be configured to determine pressure in a syringe 1904 and/or a gastric band (not shown). The syringe pressure accessory system 1900 may include the syringe 1904, a needle 1910, a display unit 1956 and a syringe accessory 1902, which may comprise a valve 1946, a disposable unit 1934 and a durable unit 1932. When properly assembled and functioning, the syringe accessory 1902 may communicate with the display unit 1956 via the durable unit 1932 to provide the obtained pressure readings and other related information such that they may be displayed on the display unit 1956. For example, the display unit 1956 may display information as to whether the valve 1946 is in an "open" or "closed" state. Additionally and/or alternatively, the display unit 1956 may display information related to whether a "self-test" conducted on the pressure accessory system 1900 was successful, and if not successful, the portions of the self-test that resulted in an error or failure. In one embodiment, a user may utilize the display unit 1956 to control the other portions of the syringe pressure accessory system 1900 (e.g., the durable unit 1932 or the valve 1946).

The syringe 1904 may, in one embodiment, be the syringe 104 of FIG. 1. The syringe 1904 may be connectable with the valve 1946. The valve 1946 may be a stand-alone component, or it may be integrated as a part of the syringe 1904 or the disposable unit 1934. The valve 1946 may function to isolate the pressure within a gastric band when the syringe pressure accessory system 1900 is in fluid communication with the gastric band, for example, when the needle 1910 is inserted into an access port of the gastric band. In one embodiment, the valve 1946 may be a manual, user-operated valve which has an "open" configuration and a "closed" configuration. When the valve 1946 is in an "open" configuration or orientation, fluid flow through the valve 1946 may occur. When the valve 1946 is in a "closed" configuration, fluid flow through the valve 1946 does not occur or is prevented. For example, fluid flow between the syringe 1904 and the rest of the syringe pressure accessory system 1900 may be prevented, thereby allowing the syringe accessory 1902 to measure the pressure within the gastric band without influence from the syringe 1904. The user may hold the syringe 1904 in one hand and may manipulate the valve 1946 to place the valve 1946 in the "open" or "closed" configuration with his or her other hand. In one embodiment, the valve 1946 may be an automatic one-way valve which allows fluid to flow from the syringe 1904 to the gastric band, while preventing fluid from the gastric band from flowing to the syringe 1904.

As shown in FIG. 19B, the valve 1946, in one embodiment, may be located between a syringe connector 1948 and a needle connector 1944. Furthermore, the valve 1946 may be in communication with the disposable unit 1934 which may include a pressure sensor 1942 for measuring pressure in the syringe 1904 and/or the gastric band (not shown) and a coupled data storage 1940 (which may be a non-transitory, tangible memory, such as a ROM, FLASH Memory, etc.) for saving calibration corrections as applicable to the pressure sensor 1942. The disposable unit 1934 may be fluidly coupled to the syringe 1904 and the gastric band (via the needle 1910) such that it may measure a pressure within the syringe 1904 and/or the gastric band. This particular configuration of the syringe pressure accessory system 1900 may minimize the number of components in the disposable unit 1934, and thereby minimize the size, weight and/or cost of the disposable unit 1934.

As shown in FIG. 19B, the disposable unit 1934 may be electrically coupled or connected to the durable unit 1932 via, for example, an electrical connection 1950.

As shown in both FIGS. 19A and 19B, the durable unit 1932 may include an "on" indicator 1920 and status lights or LEDS 1916. In addition, as shown in FIG. 19B, the durable unit 1932 may include a radio 1910, a non-coiled antenna 1912, a microcontroller 1914 of FIG. 12 and a battery 1918.

The microcontroller 1914 may be a processor and may, in one embodiment, control the operation of the durable unit 1932. The microcontroller 1914 may be connected to the status lights or LEDS 1916, which may provide a visual indication of characteristics such as pressure changes by illumination intensity, color changes and/or flashing frequency. These indications may prompt a medical professional to view and/or operate the display unit 1956 to obtain more detailed information. In one embodiment, pressure changes caused by, for example, addition or subtraction of fluid and/or peristaltic contractions from the patient swallowing a bolus may be displayed by the status lights or LEDs 1916 via changing of the colors from a first color (e.g., yellow) to a second color (e.g., blue) when the pressure change exceeds a defined threshold.

The microcontroller 1914 may also be connected to the radio 1910 and the non-coiled antenna 1912. The microcontroller 1914 may provide data to the radio 1910 for transmission to the display unit 1956 via the antenna 1912. In addition, the radio 1910 and the antenna 1912 may receive data from the display unit 1956 and may pass the received data to the microcontroller 1914.

The microcontroller 1914 may be electrically connected to the battery 1918 which may power the microcontroller 1914 and/or various other components of the durable unit 1932. The battery 1918 may be fixed and the durable unit 1932 may be disposed when the battery 1918 is depleted. Alternatively, the battery 1918 may be replaceable and/or rechargeable.

The battery 1918 may also power the "on" indicator 1920, which may be a LED or light that simply indicates that the durable unit 1932 and/or the syringe accessory 1902 are in a usable state. The "on" indicator 1920 may be configured to illuminate when the power is applied, any self tests have passed, and/or when the syringe accessory 1902 is ready to be used.

Generally, the display unit 1956 may be configured to display pressure data, among other functions. The display unit 1956 may be separated from the rest of the syringe pressure accessory system 1900. However, the display unit 1956 may communicate with certain components of the syringe pressure accessory system 1900 such as when the durable unit 1932 wirelessly sends data back and forth as needed. The display unit 1956 may include a display portion 1926 which may be a color LCD touch screen, a microcontroller 1958, a battery 1960, a data storage 1966, a radio 1968 and a non-coiled antenna 1970. These components of the display unit 1956 may be coupled to one another as shown in FIG. 19B. In addition, in one embodiment, they may function similarly to the corresponding components of the display unit 156 of FIG. 12. For example, the display portion 1926 may be the display 126 of FIG. 12, the microcontroller 1958 may be the microcontroller 158 of FIG. 12, the battery 1960 may be the power source 160 of FIG. 12, the data storage 1966 may be data storage 166 of FIG. 12 and may be configured to store data for calibrating the pressure sensor, the radio 1968 may be the radio 168 of FIG. 12 and the non-coiled antenna 1970 may be non-coiled antenna 170 of FIG. 12. While not shown in FIG. 19B, the display unit 1956 may further comprise an input and output corresponding to input 162 and output 164 of FIG. 12.

Alternatively and/or in addition, a cable (not shown) may be used to connect the display unit 1956 with the durable unit 1932. In one embodiment, where a cable is used, wireless capabilities are not needed or included. Accordingly, wireless communication components such as the radio 1910 and 1968 and the non-coiled antenna 1912 and 1970 may be eliminated to save costs. A redundant battery (e.g., the battery 1918) may also be eliminated as the cable may be configured to provide power from the display unit 1956 to the durable unit 1932.

In one embodiment, the syringe pressure accessory system 1900 may further comprise means to initiate a measurement (not shown). For example, the syringe pressure accessory system 1900 may include a physical button located on the durable unit 1932 or a user-interface button (e.g., a soft button on the touch screen display) of the display unit 1956 for initiating pressure measurement or analysis. The button may be a mechanical momentary contact, a mechanical switch, a touch-sensitive, optical or tilt-sensitive object and the like. Where means to initiate a measurement is included within the syringe pressure accessory system 1900, the valve 1946 may include a detector (not shown) for detecting whether the valve 1946 is in an "open" or "closed" configuration. The detector may be a sensor configured to detect when the valve 1946 is in a "closed" configuration, and in response, may send or emit a signal alerting the microcontroller 1914 and/or the microcontroller 1958, which may ultimately trigger and/or begin taking readings from the pressure sensor 1942. The detector may utilize an optical switch, a mechanical switch, a magnetic switch, a contact switch, and/or any other mechanism to sense whether the valve 1946 is opened or closed.

Figure 20A:
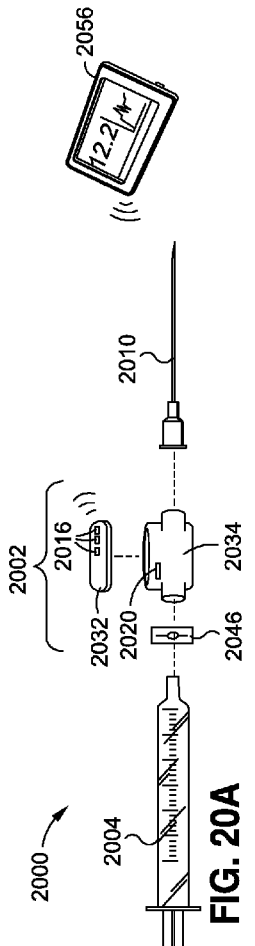
FIG. 20A illustrates a perspective, exploded view of a syringe pressure accessory system according to an embodiment of the present invention.
Figure 20B:
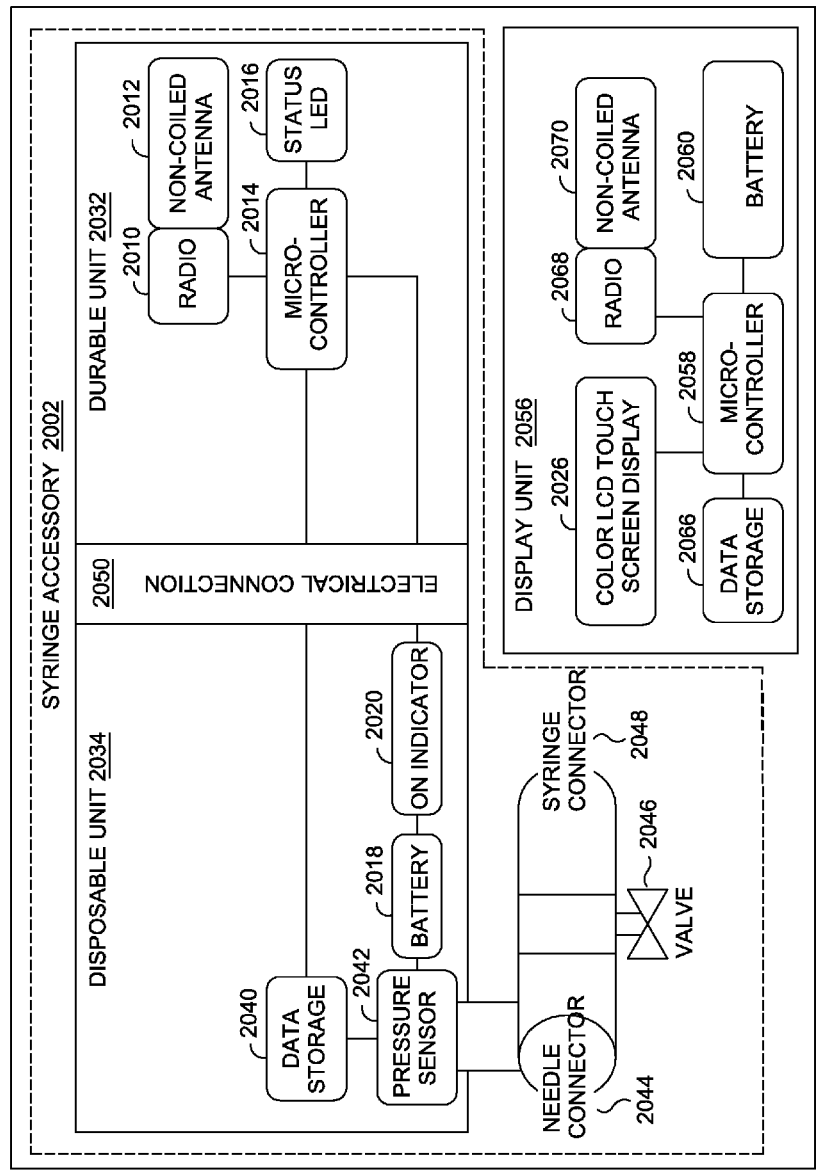
FIG. 20B illustrates a box diagram of the syringe pressure accessory system of FIG. 20A according to an embodiment of the present invention.

Turning to FIG. 20A, a syringe pressure accessory system 2000 is illustrated in an exploded view. FIG. 20B is a box diagram of the syringe pressure accessory system 2000 of FIG. 20A. As with certain other embodiments described herein, the syringe pressure accessory system 2000 may be configured to determine pressure in a syringe 2004 and/or a gastric band (not shown). The elements shown in FIGS. 20A and 20B may correspond and function similarly to the elements shown and/or described with respect to FIGS. 19A and 19B (e.g., the syringe 2004 may be the syringe 1904, a display unit 2056 may be the display unit 1956) with a few variations. For example, in this embodiment, a battery 2018 and an "on" indicator 2020 are no longer housed in a durable unit 2032, but instead are housed in a disposable unit 2034. While the overall system of the syringe pressure accessory system 2000 may operate in a similar manner as the syringe pressure accessory system 1900, by housing the battery 2018 and the "on" indicator 2020 in the disposable unit 2034, the overall life and size of the battery 2018 may be optimized since the battery 2018 may be used only once prior to disposal. In other words, a much smaller (and perhaps non-rechargeable) battery 2018 may be utilized, thereby saving space and/or cost.

Turning to FIG. 21A, a syringe pressure accessory system 2100 is illustrated in an exploded view. FIG. 21B is a box diagram of the syringe pressure accessory system 2100 of FIG. 21A. As with certain other embodiments described herein, the syringe pressure accessory system 2100 may be configured to determine pressure in a syringe 2104 and/or a gastric band (not shown). The elements shown in FIGS. 21A and 21B may correspond and function similar to the elements shown and/or described with respect to FIGS. 19A and 19B (e.g., the syringe 2104 may be the syringe 1904, a display unit 2156 may be the display unit 1956) with a few variations. For example, in this embodiment, the elements of the durable unit 1932 (e.g., the radio 1910, the microcontroller 1914, etc.) are now housed in a disposable unit 2134. In this embodiment, a durable unit is not required and may be completely eliminated as the relevant components are now housed in the disposable unit 2134. In addition, an electrical connector (e.g., the electrical connector 1950 of FIG. 19B) typically used to couple a durable unit (e.g., the durable unit 1932 of FIG. 19B) to a disposable unit (e.g., the disposable unit 1934 of FIG. 19B) may also be unnecessary and eliminated. This embodiment may provide the optimal ease of use as the medical professional may obtain a different disposable unit 2134 for each use.

Turning to FIG. 22A, a syringe pressure accessory system 2200 is illustrated in an exploded view. FIG. 22B is a box diagram of the syringe pressure accessory system 2200 of FIG. 22A. As with certain other embodiments described herein, the syringe pressure accessory system 2200 may be configured to determine pressure in a syringe 2204 and/or a gastric band (not shown). The elements shown in FIGS. 22A and 22B may correspond and function similar to the elements shown and/or described with respect to FIGS. 19A and 19B (e.g., the syringe 2204 may be the syringe 1904, a display unit 2256 may be the display unit 1956, etc.) with a few variations. For example, in this embodiment, the elements of the disposable unit 1934 (e.g., the pressure sensor 1942, the data storage 1940) are now housed in a durable unit 2232. In this embodiment, a disposable unit similar to the disposable unit 1934 is not required and may be completely eliminated as the relevant components are now housed in the durable unit 2232. Similarly, an electrical connector (e.g., the electrical connector 1950 of FIG. 19B) typically used to couple a durable unit (e.g., the durable unit 1932 of FIG. 19B) to a disposable unit (e.g., the disposable unit 1934 of FIG. 19B) may also be unnecessary and eliminated. However, in this embodiment, there is still a disposable component embodied in a disposable unit 2234. In one embodiment, as shown in FIG. 22A, the disposable unit 2234 may be utilized as a fluid conduit connecting a valve 2246, the durable unit 2232, a needle 2210 with the syringe 2204 and the gastric band. In another embodiment, as shown in FIG. 22B, the disposable component 2234 may be integrated with the valve 2246 and a membrane 2286. The membrane 2286 may be, for example, the disposable membrane 138 which may be configured such that it allows the durable unit 2232 to obtain pressure readings. The membrane 2286 may also function as a sterile barrier between the durable unit 2232 and the disposable unit 2234. Because the disposable unit 2234 of FIG. 22B comprises only the fluid-conduit components (e.g., the valve 2246, a needle connector 2244, a syringe connector 2248, and the membrane 2286) and not the pressure-reading components (e.g., a pressure sensor 2242, a battery 2218), the use and replacement of the disposable unit 2234 will likely cost less because it comprises fewer components when compared to the disposable unit 1934, 2034, and 2134, which comprise both the fluid-conduit and the pressure-reading components.

Turning to FIG. 23A, a syringe pressure accessory system 2300 is illustrated in an exploded view. FIG. 23B is a box diagram of the syringe pressure accessory system 2300 of FIG. 23A. As with certain other embodiments described herein, the syringe pressure accessory system 2300 may be configured to determine pressure in a syringe 2304 and/or a gastric band (not shown). The elements shown in FIGS. 23A and 23B may correspond and function similar to the elements shown and/or described with respect to FIGS. 19A and 19B (e.g., the syringe 2304 may be the syringe 1904) with a few variations. For example, in this embodiment, as shown in FIG. 23A, the syringe pressure accessory system 2300 may comprise a display unit 2356, a disposable unit 2334, the syringe 2304 and a needle 2310. The display unit 2356 may, in this embodiment, comprise certain components of the disposable unit 1932 and the durable unit 1934. As shown in FIG. 23B, the display unit 2356 may include a microprocessor 2314, a status LED 2316, a battery 2318, an "on" indicator 2320, a color display 2326, a data storage 2340 and a pressure sensor 2342. As the display unit 2356 may be connected to a membrane 2386, which in turn is connected to a tubing 2388, the display unit 2356 might not be remote from the disposable unit 2334. However, one advantage of this embodiment is that it includes fewer components when compared to, for example, the syringe pressure accessory system 1900 of FIGS. 19A and 19B. For example, as the display unit 2356 is configured here to include the pressure sensor 2342, a disposable unit having a pressure sensor (e.g., the disposable unit 1934) may be eliminated. Furthermore, a radio and antenna (e.g., the radios 1910 and 1968, and the non-coiled antennas 1912 and 1970) may also be eliminated. In addition, while the syringe pressure accessory system 1900 of FIGS. 19A and 19B may include multiple microcontrollers (e.g., the microcontrollers 1914 and 1958), batteries (e.g., the batteries 1918 and 1960), and so forth, the syringe pressure accessory system 2300 may utilize only one microcontroller 2314, one battery 2318, etc. However, one skilled in the art will recognize that additional microcontrollers, batteries, etc. may be included in other embodiments where the display unit 2356 includes the pressure sensor 2342.

As further shown in FIGS. 23A and 23B, the display unit 2356 may be fluidly coupled to the disposable unit 2334 via the tubing 2388. The disposable unit 2334 may include the valve 2346, a needle connector 2344 and a syringe connector 2348 for attaching the needle 2310 and the syringe 2304, respectively. When assembled, the syringe pressure accessory system 2300 may operate to obtain pressure readings similarly to one or more of the above-described embodiments of the present invention.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A system for determining a pressure of a fluid in a gastric band for the treatment of obesity, the system comprising:
    a needle having a tip and a base, the needle further having a channel between the tip and the base for carrying the fluid;
    a syringe fluidly coupled to the needle, the syringe having a plunger and a barrel; and
    a syringe pressure accessory having a first end coupled to the base of the needle and a second end coupled to the barrel of the syringe and providing a fluid path between the syringe and the needle, the syringe pressure accessory including:
        a disposable unit disposable after a single use, the disposable unit having a pressure sensor configured to access the fluid path for obtaining pressure data and a data storage coupled to the pressure sensor, the data storage configured to store pressure sensor calibration data,
        a durable unit configured to be reusable and coupled to the disposable unit, the durable unit positioned at a location outside the fluid path, the durable unit configured to analyze the obtained pressure data, the durable unit comprising:
    a microcontroller configured to control operation of the durable unit;
    a status LED coupled to the microcontroller, the status LED configured to indicate a status of the durable unit;
    a radio coupled to the microcontroller, the radio configured to send and receive signals between the durable unit and a remote display unit;
    an antenna coupled to the radio, the antenna for assisting the radio in sending and receiving the signals between the durable unit and the remote display unit;
    an on indicator coupled to the microcontroller, the on indicator configured to indicate whether the durable unit is powered; and
    a battery coupled to the microcontroller and the on indicator, the battery configured to power the microcontroller and the indicator, and
        a valve located between the syringe and the needle, the valve having an open configuration for allowing the fluid to flow through the valve and a closed configuration for preventing the fluid from flowing through the valve which isolates the pressure of the fluid and improves accuracy of the pressure data obtained by the pressure sensor.

2. The system of claim 1 wherein the durable unit further includes a physical interface configured to receive input from a user to trigger a pressure reading.

3. The system of claim 2 wherein the physical interface is a mechanical switch.

4. The system of claim 2 wherein the valve may further include a detector configured to detect whether the valve is in the open configuration or the closed configuration, the detector further configured to trigger the pressure sensor to begin obtaining the pressure reading when the valve is in the closed configuration.

5. The system of claim 4 wherein the detector is a switch for sensing whether the valve in the open configuration or the closed configuration.

6. The system of claim 1 wherein the status LED is configured to provide a visual indication of a pressure change.

7. The system of claim 6 wherein the status LED provides the visual indication of the pressure change by changing illumination intensity, changing a color or changing a flashing frequency when the pressure change exceeds a predefined threshold.

8. A system for determining a pressure of a fluid in a gastric band for the treatment of obesity, the system comprising:
- a needle having a tip and a base, the needle further having a channel between the tip and the base for carrying the fluid;
- a syringe fluidly coupled to the needle, the syringe having a plunger and a barrel; and
- a syringe pressure accessory having a first end coupled to the base of the needle and a second end coupled to the barrel of the syringe and providing a fluid path between the syringe and the needle, the syringe pressure accessory including:
  - a disposable unit disposable after a single use, the disposable unit having
  - a pressure sensor configured to access the fluid path for obtaining pressure data,
  - a data storage coupled to the pressure sensor, the data storage configured to store pressure sensor calibration data;
  - a battery coupled to the pressure sensor and the microcontroller, the battery configured to power the microcontroller; and
  - an on indicator coupled to the microcontroller and the battery, the on indicator configured to indicate whether the disposable unit is powered;
  - a durable unit comprising:
  - a microcontroller configured to control operation of the durable unit;
  - a status LED coupled to the microcontroller, the status LED configured to indicate a status of the durable unit;
  - a radio coupled to the microcontroller, the radio configured to send and receive signals between the durable unit and a remote display unit; and
- an antenna coupled to the radio, the antenna for assisting the radio in sending and receiving the signals between the durable unit and the remote display unit configured to be reusable and coupled to the disposable unit, the durable unit positioned at a location outside the fluid path, the durable unit for analyzing the obtained pressure data, and
  - a valve located between the syringe and the needle, the valve having an open configuration for allowing the fluid to flow through the valve and a closed configuration for preventing the fluid from flowing through the valve which isolates the pressure of the fluid and improves accuracy of the pressure data obtained by the pressure sensor.

* * * * *